United States Patent
Agar et al.

(10) Patent No.: US 10,711,261 B2
(45) Date of Patent: Jul. 14, 2020

(54) TETHERING CYSTEINE RESIDUES USING CYCLIC DISULFIDES

(71) Applicant: Brandeis University, Waltham, MA (US)

(72) Inventors: Jeffrey N. Agar, Newton, MA (US); Joseph Salisbury, Cranston, RI (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 15/753,319

(22) PCT Filed: Aug. 17, 2016

(86) PCT No.: PCT/US2016/047395
§ 371 (c)(1),
(2) Date: Feb. 18, 2018

(87) PCT Pub. No.: WO2017/031226
PCT Pub. Date: Feb. 23, 2017

(65) Prior Publication Data
US 2018/0237763 A1     Aug. 23, 2018

Related U.S. Application Data

(60) Provisional application No. 62/206,316, filed on Aug. 18, 2015.

(51) Int. Cl.
| | |
|---|---|
| *C12N 9/96* | (2006.01) |
| *C12N 9/02* | (2006.01) |
| *C07K 19/00* | (2006.01) |
| *A61K 31/095* | (2006.01) |
| *A61K 31/385* | (2006.01) |
| *C12N 9/80* | (2006.01) |
| *A61K 38/00* | (2006.01) |

(52) U.S. Cl.
CPC .............. *C12N 9/96* (2013.01); *A61K 31/095* (2013.01); *A61K 31/385* (2013.01); *C07K 19/00* (2013.01); *C12N 9/0089* (2013.01); *C12N 9/80* (2013.01); *C12Y 115/01001* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,013,663 A | 1/2000 | Fujita et al. | |
| 6,046,228 A | 4/2000 | Rice et al. | |
| 2010/0093977 A1 | 4/2010 | Baker et al. | |
| 2010/0317608 A1 | 12/2010 | Garner et al. | |
| 2012/0134978 A1 | 5/2012 | Agar | |

FOREIGN PATENT DOCUMENTS

WO     2014078623 A2     5/2014

OTHER PUBLICATIONS

Jain RK, "Barriers to Drug Delivery in Solid Tumors," Scientific American, 1994, 58-65.*
Gura T, "Systems for Identifying New Drugs Are Often Faulty," Science, 1997, 278: 1041-1042.*
Auerbach R, Akhtar N, Lewis RL, Shinners BL, "Angiogenesis assays: Problems and pitfalls," Cancer and Metastasis Reviews, 2000, 19: 167-172.*
Clinical Aspects of Cancer from Merck manual, pp. 1-4. Accessed Mar. 5, 2008.*
Introduction to Cancer from Merck manual, p. 1. Accessed Mar. 5, 2008.*
"Cancer." MedLine Plus. (2009). Accessed Mar. 17, 2009. <http://www.nlm.nih.gov/medlineplus/cancer.html>.*
Sausville et al. "Contributions of Human Tumor Xenografts to Anticancer Drug Development." Cancer Res. 2006, 66(7), Apr. 1, 2006.*
Johnson et al. "Relationships between drug activity in NCI preclinical in vitro and in vivo models and early clinical trials." British Journal of Cancer (2001), 84(10), 1424-1431.*
Lala et al. "Role of nitric oxide in tumor progression: Lessons from experimental tumors." Cancer and Metastasis Reviews (1998), 17(1), 91-106.*
Golub et al. "Molecular Classification of Cancer: Class Discovery and Class Prediction by Gene Expression Monitoring." Science ( 1999), vol. 286, 521-537.*
"Alzheimer's disease." CNN Health, Obtained Oct. 9, 2010, URL:http://www.cnn.com/2003/HEALTH/conditions/09/24/alzheimers.drug.ap/index.html.*
Antonio R. Damasio, Alzheimer's Disease and Related Dementias, Cecil Textbook of Medicine, 20th edition (1996), vol. 2, pp. 1992-1996.*
Auclair et al., "Strategies for stabilizing superoxide dismutase (SOD1), the protein destabilized in the most common form of familial amyotrophic lateral sclerosis", Proceedings of the National Academy of Sciences, vol. 107, No. 50, Dec. 14, 2010, pp. 21394-21399, XP055266790, US.
Erlanson et al., "Tethering: Fragment-Based Drug Discovery", Jan. 1, 2009, XP055266987, Retrieved from the Internet: URL:http://www-nmr.cabm.rutgers.edu/academics/biochem694/2009BioChem412/2009Presentations/CurtSchauder.pdf [retrieved on Apr. 20, 2016].

(Continued)

*Primary Examiner* — Alicia L Otton
(74) *Attorney, Agent, or Firm* — Michele M. Wales; Inhouse Patent Counsel, LLC

(57) ABSTRACT

Described herein are compounds and methods for tethering proteins. For example, dimers of Protein X listed in Table 1 are described, where the dimers are formed by the covalent bonding of a cysteine on the first monomer to a cysteine on the second monomer via a cyclic disulfide linker. The covalently attached dimers exhibit increased stabilization and can be used to treat neurodegenerative diseases (such as, for example, Parkinson's Disease, ALS, Alzheimer's Disease, Huntington's Disease, Epilepsy, Frontotemporal Dementia, and/or DMD), cancer, autoimmune disease, and/or Celiac disease.

21 Claims, 6 Drawing Sheets

(56) References Cited

OTHER PUBLICATIONS

Erlanson et al., "Tethering: Fragment-Based Drug Discovery", Annual Review of Biophysics and Biomolecular Structure, Annual Reviews Inc., Palo Alto, CA, US, vol. 33, Jan. 1, 2004, pp. 199-223, XP008069432.
European Search Report from EP 13854478.8, dated May 4, 2016.
Hardy, "Chapter 17. A Link Means a Lot: Disulfide Tethering in Structure-Based Drug Design" In: "Computational and Structural Approaches to Drug Discovery Ligand-Protein Interactions", Jan. 1, 2007, Royal Society of Chemistry, Cambridge, UK, XP055266983.
International Search Report dated May 12, 2014, from PCT / US2013/070239.
Isaac et al., "Nucleophilic reactivity of Zinc-bound thiolates: subtle interplay between coordination set and conformational flexibility", Chemical Science, vol. 3, No. 12, Jan. 1, 2012, p. 3409, XP055266928,United Kingdom.
Japanese Office Action dated Oct. 24, 2017 in Japanese Application No. 2015-542801.
Logan et al., "Engineered Disulfide Bonds Restores Chaperone Like Function of DJ-1 Mutants Linked to Familial Parkinson's Disease," Biochemistry, 49(27):5624-5633 (2010).
Williams, B. "Disulfide-Mediated Stabilization of DJ-1, a Protein Implicated in Parkinson Disease" Honors Thesis, May 1, 2013 (May 1, 2013), XP055308842, Retrieved from the Internet: URL:http://bir.brandeis.edu/bitstream/handle/10192/25232/WilliamsThesis2013.pdf?sequence=I [retrieved on Oct. 10, 2016] the whole document.
Written Opinion and International Search Report dated Oct. 21, 2016 in PCT/US2016/047395.
International Preliminary Report on Patentability dated Mar. 1, 2018 and received in PCT/US2016/047395.
Office Action dated Nov. 29, 2019 received in Application No. 16 758 328.5.

\* cited by examiner

NSC54128

NSC72270

NSC56224

NSC72272

NSC62632

NSC185355

NSC624157

NSC90788

NSC663605

NSC212561

NSC5391

NSC72268

NSC56224

TETHERING CYSTEINE RESIDUES USING CYCLIC DISULFIDES

CROSS-REFERENCE TO RELATED APPLICATIONS

This application is a § 371 National Stage Application of PCT/US16/47395 filed on Aug. 17, 2016, which claims priority to U.S. 62/206,316 filed on Aug. 18, 2015. Both of these documents are hereby incorporated by reference in their entirety.

BACKGROUND OF THE INVENTION

Many therapeutic molecules form covalent bonds with cysteine residues on their protein targets. The mechanisms of the majority of these molecules were either elucidated long after development or are not fully understood. Recent successful drug discovery efforts, however, moved to structure-based design. These require both an accurate structural model of the target protein and a high-specificity ligand.

One third of therapeutic molecules, including many blockbuster drugs, form covalent bonds with their targets. These electrophilic drugs generally bond to a nucleophilic amino acid, often serine or cysteine, on a target protein. Aspirin and penicillin (and their many derivatives) acylate serines and numerous drugs form covalent bonds with specific cysteines. These therapeutic agents are effective despite the potential for off-target reactions with hundreds of highly reactive, nucleophilic residues, which are often required for the function of essential proteins. A worst case scenario for reaction with the "wrong" nucleophile is nerve gases (e.g., Sarin, intravenous $LD_{50}$~30 µg/kg), which covalently modify the active site serine of acetylcholine esterase. On the other hand, comparable toxicity has been harnessed to selectively target cancer cells-bortezomib/Velcade ($LD_{100}$<250 µg/kg) selectively modifies an active site threonine of the proteasome. Unintended reaction with a highly reactive nucleophile isn't necessarily disastrous—it has led to a drug. The disulfide-containing substance, disulfiram, was intended to treat parasitic infections, but when tested on humans gave severe "hangover" symptoms upon alcohol consumption. Years after its therapeutic use began, this compound, dubbed antabuse, was found to bind the highly reactive active site cysteines of alcohol dehydrogenase. Nevertheless, the paucity of therapeutic suicide inhibitors to most human proteases, which (unlike viral proteases) have numerous homologues with identical off-target catalytic sites, has been attributed to off-target nucleophiles.

With effective covalent drugs, off-target binding tends to be offset by selectivity for the target and the enhanced potency inherent to irreversible inhibition. The uncanny specificities of cysteine-binding therapeutics involve elegant and usually serendipitous chemistry. The gastroesophageal reflux disease drugs (GERD, e.g., omeprazole/Prilosec™ lansoprazole/Prevacid™, etc.) use a cyclic sulphenamide to irreversibly bind a cysteine residue of the proton pump of the intestinal lumen. These benzolamide-derivative prodrugs require protonation of a low pKa pyridine nitrogen (pKa<4.5) for activation and sequestration. They are neutral, inactive, and permeable, but are activated upon encountering the pH~0.8 parietal cell canaliculus, which contains their target (i.e., the proton pump). Here, they accumulate at 1000-fold higher concentrations. While the chemical basis of proton-mediated accumulation of omeprazole was appreciated, if not designed, the elegant sulfur-based chemistry behind activation and binding of a target cysteine was serendipitous.

The antithrombosis factors clopidogrel/Plavix™, ticlopide/Ticlid, etc. are also prodrugs. Activation by cytochrome P450 enzymes results in the scission of a ring carbon-sulfur bond, creating a sulfhydryl group that can then form a disulfide bond with its target cysteine on the adenosine diphosphate (ADP) chemoreceptor $P2Y_{12}$. In addition to increased specificity for its target, which it permanently inactivates, the active metabolite has improved plasma protein binding characteristics. The thrombosis drugs had their beginnings in functional assays, and fortunately animal studies, because the active metabolite is not produced in most cell-based assays. Both their mechanism of action and target were unknown at the time of discovery.

More recent compounds employing sulfhydryl moieties were rationally designed. Dacomitinib, afatinib, and neratinib are EGFR kinase inhibitors with a high-affinity, nucleotide-analogue moiety that reversibly binds the ATP-binding pockets of numerous kinases and a second moiety designed to covalently bond with a non-conserved cysteine (present in EGFR but not its homologues). The electrophilic moiety is purposefully a low-reactivity acrylamide to minimize off-target reactions. A related chemical approach used low-reactivity, acrylamide-based, electrophiles to target non-conserved (in humans) and non-catalytic-residue cysteine of the HCV NS3/4A viral protease (HCVP).

In sum, all known approaches either minimize the exposure of highly reactive electrophiles ("hiding" a reactive sulfur in disulfides or in rings), or minimize the reactivity of exposed electrophiles (using acrylamide adducts). Unfortunately, however, the specificity of sulphenamides depends upon an acidic environment (pH<4.5) found only in the intestinal lumen, and the specificity of therapeutics employing reactive sulfhydryl groups is poorly understood. A few therapeutic molecules were obtained by rationally attaching low-reactivity electrophiles to high affinity and specificity moieties. Unfortunately, compounds with high affinity and specificity tend to appear in the final stages of a drug development effort making this approach best suited for improving existing specificity.

There exists a need for a strategy for conferring specificity to drugs that target cysteine, in general, but pairs of cysteine, in particular.

SUMMARY OF THE INVENTION

Representative Methods of the Invention

In certain embodiments, the invention relates to a method comprising the step of contacting a compound of Formula I or a compound of Formula II with a first Protein X and a second Protein X under conditions suitable for cross-linking the first Protein X to the second Protein X, wherein the first Protein X comprises a first cysteine residue; the second Protein X comprises a second cysteine residue; the compound of Formula I is

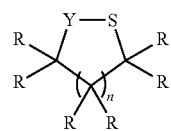

Wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and the compound of Formula II is

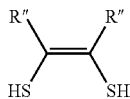

II wherein R" is —H, alkyl, or aryl, or both R", taken together, form a ring; wherein any alkyl, aryl, or ring may be substituted with —OH, alkyl, or halo and wherein the first and the second Protein X are selected from Table 1.

In certain embodiments, the invention relates to a method comprising the step of contacting a compound with a first Protein X and a second Protein X under conditions suitable for cross-linking the first Protein X to the second Protein X, wherein the first Protein X and the second Protein X are at least 80%, 85%, 86%, 87%, 88%, 89%, 90%, 91%, 92%, 93%, 94%, 95%, 96%, 97%, 98%, 99% or 100% homologous or identical to any one of the Protein X listed in Table 1 (in preferred embodiments, the first Protein X and the second Protein X are derived from the same Protein X); and the compound is a compound of Formula I

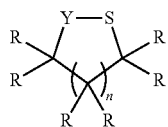

I wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl.

In certain embodiments, the invention relates to a method comprising the step of contacting a compound with a first Protein X and a second Protein X under conditions suitable for cross-linking the first Protein X to the second Protein X, wherein the first Protein X and the second Protein X is at least 80%, 85%, 86%, 87%, 88%, 89%, 90%, 91%, 92%, 93%, 94%, 95%, 96%, 97%, 98%, 99% or 100% homologous or identical to any one of the Protein X listed in Table 1 (in preferred embodiments, the first Protein X and the second Protein X are derived from the same Protein X); and the compound is a compound of Formula II

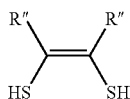

II wherein R" is —H, alkyl, or aryl, or both R", taken together, form a ring; wherein any alkyl, aryl, or ring may be substituted with —OH, alkyl, or halo.

In certain embodiments, the invention relates to a method of treating or preventing a Disease Y listed in Table 1 for each Protein X, comprising the step of administering to a subject in need thereof a therapeutically effective amount of a compound of Formula I or a compound of Formula II, wherein the compound of Formula I is

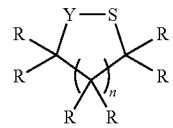

I wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and the compound of Formula II is

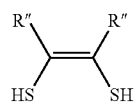

II wherein R" is —H, alkyl, or aryl, or both R", taken together, form a ring; wherein any alkyl, aryl, or ring may be substituted with —OH, alkyl, or halo.

In certain embodiments, the invention relates to a method of treating or preventing a Disease Y listed in Table 1 for each Protein X, comprising the step of administering to a subject in need thereof a therapeutically effective amount of a stabilized analogue of Protein X, wherein said analogue has a tertiary structure and comprises a first monomer of Protein X and a second monomer of the Protein X; wherein the first monomer of Protein X comprises a first cysteine residue; the second monomer of Protein X comprises a second cysteine residue; the first cysteine residue is connected to the second cysteine residue by a connection; and the connection is a connection of Formula III or a connection of Formula IV, wherein Formula III is

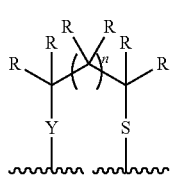

III wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and Formula IV is

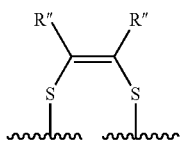

wherein R" is —H, alkyl, or aryl, or both R", taken together, form a ring; wherein any alkyl, aryl, or ring may be substituted with —OH, alkyl, or halo. In preferred embodiments, the first Protein X and the second Protein X are at least 80%, 85%, 86%, 87%, 88%, 89%, 90%, 91%, 92%, 93%, 94%, 95%, 96%, 97%, 98%, 99% or 100% homologous or identical to any one of the Protein X listed in Table 1. In further preferred embodiments, the first Protein X and the second Protein X are derived from the same Protein X.

In certain embodiments, the invention relates to a compound of Formula I

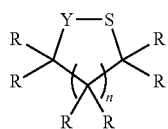

wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl.

One aspect of the invention is a stabilized analogue of Protein X, wherein said analogue has a tertiary structure and comprises a first monomer of Protein X and a second monomer of the Protein X; wherein the first monomer of Protein X comprises a first cysteine residue; the second monomer of Protein X comprises a second cysteine residue; the first cysteine residue is connected to the second cysteine residue by a connection; and the connection is a connection of Formula III or Formula IV:

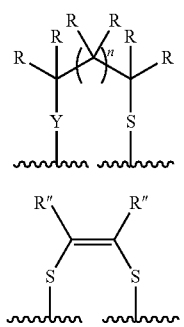

wherein Y is S, S=O, or S(=O)$_2$; n is 0, 1, 2, 3, or 4; R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and R" is —H, alkyl, or aryl, or both R", taken together, form a ring; wherein any alkyl, aryl, or ring may be substituted with —OH, alkyl, or halo. In preferred embodiments, the first Protein X and the second Protein X are at least 80%, 85%, 86%, 87%, 88%, 89%, 90%, 91%, 92%, 93%, 94%, 95%, 96%, 97%, 98%, 99% or 100% homologous or identical to any one of the Protein X listed in Table 1. In further preferred embodiments, the first Protein X and the second Protein X are derived from the same Protein X. In certain embodiments, these stabilized analogues are used to treat or prevent a Disease Y listed in Table 1 for each Protein X by administering to a subject in need thereof a therapeutically effective amount of a stabilized analogue of Protein X.

BRIEF DESCRIPTION OF THE FIGURES

FIG. 1 depicts a) a potential reaction mechanism where a cyclic disulfide reacts with the cysteine of one monomer and the resulting thiolate can then react with, for example, a hydrogen peroxide-modified thiolate on the other monomer (Isaac, et al. Chemical Science 2012); b) side-chains of Cys53's in the dimer interface of DJ-1 (PDB: 3SF8), demonstrating their close spacing (Premkumar, et al. J. Struct. Biol. 2011, 176, 414). The appearance of Cys111's in the dimer interface of SOD1 is very similar.

DETAILED DESCRIPTION OF THE INVENTION

Overview

Figure 1:
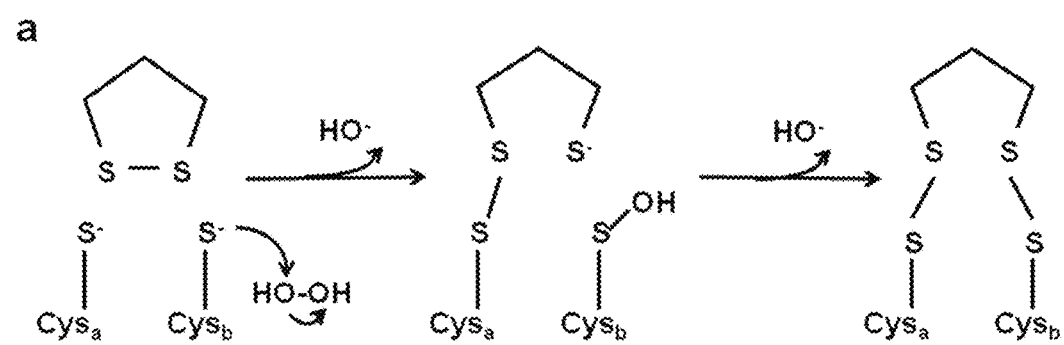
Figure 1:
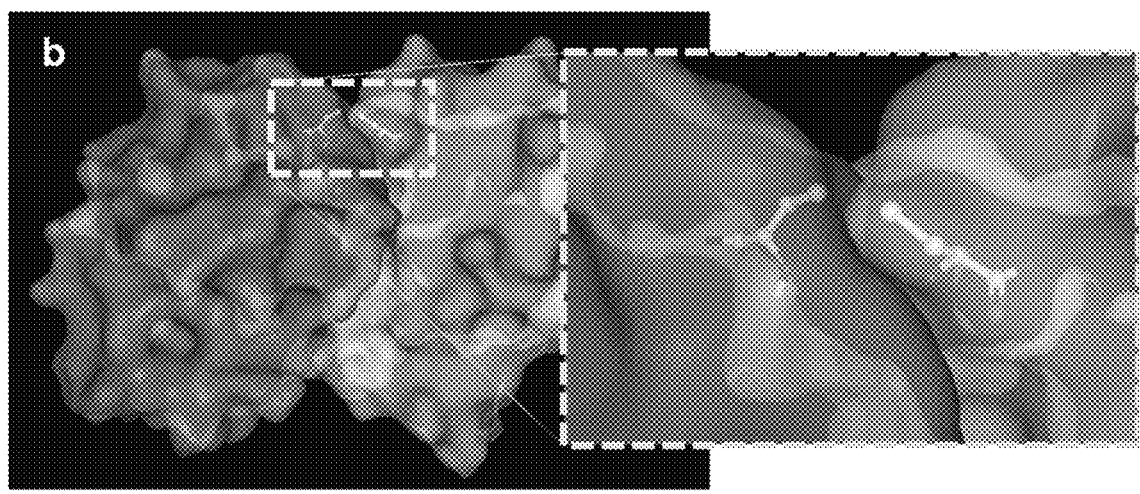

The covalent attachment of molecules can be used to affect protein structure and function. Covalently attached molecules can be used to inhibit, promote activity, stabilize, and destabilize proteins and peptides. One problem is encoding adequate specificity in covalent binders for the intended target. In certain embodiments, the invention relates to chemical tools, cyclic disulfides, which target pairs of cysteine residues and significantly enhance the specificity for pairs of cysteine over lone cysteine residues. In addition to augmenting current approaches to rational design, cyclic disulfides offer a launching point for compound optimization for novel targets. Whereas previous approaches to covalent modification tended to be devoted to inactivation of an enzyme, cyclic disulfides are also amenable to protein (including enzyme) stabilization. We apply cyclic-disulfides to the stabilization of any one of the Protein X listed in Table 1 involved in diseases, such as, for example, Disease Y shown in Table 1. In preferred embodiments, the disease that can be treated using the compounds disclosed herein, include, but are not limited to neurodegenerative disease (such as, for example, Parkinson's Disease, ALS, Alzheimer's Disease, Huntington's Disease, Epilepsy, Frontotemporal Dementia, and/or DMD), cancer, autoimmune disease and/or Celiac disease.

Table 1 shows a consolidated list of protein targets (Protein X) that can form the cyclic disulfide connections to form the stabilized analogues as described in herein. Column 1 lists the "Protein X" of each protein target that can be used to derive the stabilized analogues described herein. Column 2 provides the "Accession Number" corresponding to the protein target listed in Column 1 and connects the Protein X to the publicly available information known about each Protein X. Additionally, the Accession Number is unique identifier used in the art that provides sequence information for each protein listed in Column 1. Column 3 describes "Disease Y" for each Protein X. Each Disease Y has been shown to be associated with each Protein X as demonstrated in Column 4 Here, "Exemplified References" provides literature evidence associating each Protein X with Disease Y.

TABLE 1

Summary Table of Protein Targets and their Associated Diseases

| Protein X | Accession Number (Homo sapiens) | Disease Y | Exemplified References |
|---|---|---|---|
| DJ-1 (Protein deglycase, also known as Parkinson disease protein 7) | BAB71782 | Parkinson's Disease | Lev N et al., "A DJ-1 Based Peptide Attenuates Dopaminergic Degeneration In Mice Models Of Parkinson's Disease Via Enhancing Nrf2," PLoS ONE 10(5): e0127549 (2015). Bonifati et al., "Mutations In The DJ-1 Gene Associated With Autosomal Recessive Early-Onset Parkinsonism," Science. 2003 Jan. 10; 299 (5604): 256-9. van der Merwe C1 et al., "Evidence For A Common Biological Pathway Linking Three Parkinson's Disease-Causing Genes: Parkin, PINK1 And DJ-1," Eur J Neurosci. 2015 May; 41(9): 1113-25. Choi et al., "Oxidative damage of DJ-1 is linked to sporadic Parkinson and Alzheimer diseases," J Biol Chem. 2006 Apr. 21; 281(16): 10916-24. Epub 2006 Mar. 3. |
| | | Amyotrophic lateral sclerosis (ALS) | Lev et al., "DJ-1 knockout augments disease severity and shortens survival in a mouse model of ALS," PLoS One. 2015 Mar. 30; 10(3): e0117190. doi: 10.1371/journal.pone.0117190. eCollection 2015. Knippenberg et al., "Altered expression of DJ-1 and PINK1 in sporadic ALS and in the SOD1(G93A) ALS mouse model," J Neuropath Exp Neurol. 2013 November; 72(11): 1052-61. doi: 10.1097/NEN.0000000000000004. |
| | | Cancer; breast cancer; laryngeal cancer. | Cao et al., "DJ-1 as a human oncogene and potential therapeutic target," Biochem Pharmacol. 2015 Feb. 1; 93(3): 241-50. doi: 10.1016/j.bcp.2014.11.012. Epub 2014 Dec. 11. Tanti et al., "SG2NA enhances cancer cell survival by stabilizing DJ-1 and thus activating Akt," Biochem Biophys Res Commun. 2015 May 27. pii: S0006-291X(15)00992-4. doi: 10.1016/j.bbrc.2015.05.069 Kawate et al., "High levels of DJ-1 protein and isoelectric point 6.3 isoform in sera of breast cancer patients," Cancer Sci. 2015 Apr. 13. doi: 10.1111/cas.12673. Zhu et al., "DJ-1-induced phosphatase and tensin homologue downregulation is associated with proliferative and invasive activity of laryngeal cancer cells," Mol Med Rep. 2015 Apr. 15. doi: 10.3892/mmr.2015.3617. Ismail et al., "DJ-1 upregulates breast cancer cell invasion by repressing KLF17 expression," Br J Cancer. 2014 Mar. 4; 110(5): 1298-306. doi: 10.1038/bjc.2014.40. Epub 2014 Feb. 6. |
| | | Alzheimer's Disease | Choi et al., "Oxidative damage of DJ-1 is linked to sporadic Parkinson and Alzheimer diseases," J Biol Chem. 2006 Apr. 21; 281(16): 10916-24. Epub 2006 Mar. 3. |
| SOD-1 | AAB27562.1 | Amyotrophic lateral sclerosis (ALS) | Valentine et al., "Misfolded CuZnSOD and amyotrophic lateral sclerosis," Proc Natl Acad Sci USA. 2003 Apr. 1; 100(7): 3617-3622. Pasinelli et al., "Amyotrophic lateral sclerosis-associated SOD1 mutant proteins bind and aggregate with Bcl-2 in spinal cord mitochondria," Neuron 2004 July; 43(1): 19-30. Rosen et al., "Mutations in Cu/Zn superoxide dismutase gene are associated with familial amyotrophic lateral sclerosis," Nature. 1993 March; 362(6415): 59-62. Bandmann et al., "Sequence of the superoxide dismutase 1 (SOD 1) gene in familial Parkinson's disease," J Neurol Neurosurg Psychiatry. 1995 July; 59(1): 90-91. |
| | | Parkinson's Disease | |
| | | Alzheimer's Disease | Zemlan et al., "Superoxide dismutase activity in Alzheimer's disease: possible mechanism for paired helical filament formation," Brain Res. 1989 Jan. 2; 476(1): 160-2. Murakami et al., "SOD1 (Copper/Zinc superoxide dismutase) deficiency drives amyloid beta protein oligomerization and memory loss in mouse model of Alzheimer Disease," J Biol Chem. 2011 December; 286(52): 44557-68. |
| Transglutaminase | BAA14329.1 | Celiac disease | Frulio et al., "Evaluating diagnostic accuracy of anti-tissue Transglutaminase IgA antibodies as first screening for Celiac Disease in very young children," Clin Chim Acta. 2015 Jun. 15; 446: 237-40. doi: 10.1016/j.cca.2015.04.035. Epub 2015 May 2. Zamot et al., "Presence of tissue transglutaminase IgA antibody as a celiac disease marker in a sample of patients with irritable bowel syndrome," P R Health Sci J. 2015 March; 34(1): 38-9. Cardoso et al., "Transglutaminase 2 interactions with extracellular matrix proteins as probed with celiac disease autoantibodies," FEBS J. 2015 June; 282(11): 2063-75. doi: 10.1111/febs.13276. Epub 2015 |

TABLE 1-continued

Summary Table of Protein Targets and their Associated Diseases

| Protein X | Accession Number (Homo sapiens) | Disease Y | Exemplified References |
|---|---|---|---|
| | | | Apr. 13.<br>Webb et al., "Celiac disease can be predicted by high levels of anti-tissue transglutaminase antibodies in population-based screening," J Pediatr Gastroenterol Nutr. 2015 June; 60(6): 787-91. doi: 10.1097/MPG.0000000000000688.<br>Klock et al., "Role of transglutaminase 2 in Celiac disease pathogenesis," Semin Immunopathol. 2012 JULY; 34(4): 513-522. Published online 2012 Mar. 22. doi: 10.1007/s00281-012-0305-0.<br>Di Sabtino et al., "The function of tissue transglutaminase in celiac disease," Autoimmun Rev. 2012 August; 11(10): 746-53. doi: 10.1016/j.autrev.2012.01.007. Epub 2012 Feb. 3. |
| | | Huntington's Disease | Karpuj et al., "Evidence for a role for transglutaminase in Huntington's disease and the potential therapeutic implications," Neurochem Int. 2002 January; 40(1): 31-6.<br>Mastroberardino et al., "Type 2 transglutaminase in Huntington's disease: a double-edged sword with clinical potential," J Intern Med. 2010 November; 268(5): 419-31. doi: 10.1111/j.1365-2796.2010.02275.x.<br>Kahlem et al., "Transglutaminase Action Imitates Huntington's Disease: Selective Polymerization of Huntingtin Containing Expanded Polyglutamine," Mol Cell. 1998 March; 1(4): 595-601. |
| | | Parkinson's Disease | Vermes et al., "Elevated concentration of cerebrospinal fluid tissue transglutaminase in Parkinson's disease indicating apoptosis," Mov Disord. 2004 October; 19(10): 1252-4.<br>Junn et al., "Tissue transglutaminase-induced aggregation of alpha-synuclein: Implications for Lewy body formation in Parkinson's disease and dementia with Lewy Bodies," Proc Natl Acad Sci USA. 2003 Feb. 18; 100(4): 2047-2052. Published online 2003 Feb. 7. doi: 10.1073/pnas.0438021100.<br>Andringa et al., "Tissue transglutaminase catalyzes the formation of alpha-synuclein crosslinks in Parkinson's disease," FASEB J. 2004 May; 18(7): 932-4. Epub 2004 Mar. 4. |
| Tau | NP_058519.3 (for isoform 1) | Alzheimer's Disease | Brunden et al., "Advances in Tau-focused drug discovery for Alzheimer's disease and related tauopathies," Nat Rev Drug Discov. 2009 October; 8(10): 783-793. doi: 10. 1038/nrd2959.<br>Mandelkow et al., "Tau in Alzheimer's disease" Trends Cell Biol. 1998 November; 8(11): 425-7. |
| | | Parkinson's Disease | Lei et al., "Tau protein: Relevance to Parkinson's disease," Int J Biochem Cell Biol. 2010 November; 42(11):1775-8. doi: 10.1016/j.biocel.2010.07.016. Epub 2010 Aug. 1.<br>Wray et al., "A tangled web- Tau and sporadic Parkinson's disease," Front Psychiatry. 2010; 1: 150. Published online 2010 Dec. 27. doi: 10.3389/fpsyt.2010.00150<br>Irwin et al., "Parkinson's disease dementia: convergence of α-synuclein, tau and amyloid-β pathologies," Nat Rev Neurosci. 2013 September; 14(9): 626-36. doi: 10.1038/nrn3549. Epub 2013 Jul. 31. |
| | | Epilepsy | Holth et al., "Tau loss attenuates neuronal network hyperexcitability in mouse and Drosophila genetic models of epilepsy," J Neurosci. 2013 Jan. 23; 334(4): 1651-1659. doi: 10.1523/JNEUROSCI.3191-12.2013.<br>DeVos et al., "Antisense reduction of Tau in adult mice protects against seizures," J Neurosci. 2013 Jul. 31; 33(31): 12887-12897. |
| Progranulin | AAH00324 (Accession Number of granulin; Progranulin is the precursor of granulin) | Alzheimer's Disease | Perry et al., "Progranulin mutations as risk factors for Alzheimer disease," JAMA Neurol. 2013 June; 70(6): 774-8. doi: 10.1001/2013.jamaneurol.393.<br>D'Alton et al., "Understanding the role of progranulin in Alzheimer's disease," Nat Med. 2014 October; 20(10): 1099-100. doi: 10.1038/nm.3712.<br>Antonell et al., "Serum progranulin levels in patients with frontotemporal lobar degeneration and Alzheimer's disease: detection of GRN mutations in a Spanish cohort," J Alzheimers Dis. 2012; 31(3): 581-91. doi: 10.3233/JAD-2012-112120. |
| | | Frontotemporal Dementia | Antonell et al., "Serum progranulin levels in patients with frontotemporal lobar degeneration and Alzheimer's disease: detection of GRN mutations in a Spanish cohort," J Alzheimers Dis. 2012; 31(3): 581-91. doi: 10.3233/JAD-2012-112120.<br>Almeida et al., "Progranulin, a glycoprotein deficient in frontotemporal dementia, is a novel substrate of several protein disulfide isomerase family proteins," PLoS One. 2011; 6(10): e26454. Published online 2011 Oct. 18. doi: 10,1371/journal.pone.0026454.<br>Chiang et al., "Progranulin mutation causes frontotemporal dementia in the Swedish Karolinska |

TABLE 1-continued

Summary Table of Protein Targets and their Associated Diseases

| Protein X | Accession Number (Homo sapiens) | Disease Y | Exemplified References |
|---|---|---|---|
| | | Cancer; small cell lung cancer; cervical cancer; gastrointestinal cancer. | *family*," Alzheimers Dement. 2008 November; 4(6): 414-20. doi: 10.1016/j.jalz.2008.09.001.<br>Edelman et al., "*GP88 (progranulin): a novel tissue and circulating biomarker for non-small cell lung carcinoma*," Hum Pathol. 2014 September; 45(9): 1893-9. doi: 10.1016/j.humpath.2014.05.011. Epub 2014 Jun. 5.<br>Wei et al., "*Elevated expression of secreted autocrine growth factor progranulin increases cervical cancer growth*," Cell Biochem Biophys. 2015 January; 71(1): 189-93. doi: 10.1007/s12013-014-0183-2.<br>Lu et al., "*Growth factor progranulin contributes to cervical cancer cell proliferation and transformation in vivo and in vitro.*," Gynecol Oncol. 2014 August; 134(2): 364-71. doi: 10.1016/j.ygyno.2014.05.025. Epub 2014 Jun. 3.<br>Hu et al., "*Progranulin promotes tumour necrosis factor-induced proliferation of suppressive mouse CD4+Foxp3+ regulatory T cells*," Immunology. 2014 June; 142(2): 193-201. doi: 10.1111/imm.12241.<br>Demorrow. "*Progranulin: a novel regulator of gastrointestinal cancer progression*," Transl Gastrointest Cancer. 2013 July; 2(3): 145-151. |
| snRNP SM D3 | NP_004166 | Autoimmune disease | Mahler. "*Sm peptides in differentiation of autoimmune diseases*," Adv Clin Chem. 2011; 54: 109-28.<br>Zieve et al., "*The anti-Sm immune response in autoimmunity and cell biology*," Autoimmun Rev. 2003 September; 2(5): 235-40.<br>McClain et al., "*Anti-sm autoantibodies in systemic lupus target highly basic surface structures of complexed spliceosomal autoantigens*," J Immunol. 2002 Feb. 15; 168(4): 2054-62. |
| Galectin-1 | NP_002296.1 | Cancer; pancreatic cancer; bladder cancer; breast cancer. | Thijssen et al., "*Galectin expression in cancer diagnosis and prognosis: A systematic review*," Biochim Biophys Acta. 2015 April; 1855(2): 235-247. doi: 10.1016/j.bbcan.2015.03.003. Epub 2015 Mar. 25.<br>Martinez-Bosch et al., "*Targeting Galectin-1 in pancreatic cancer: immune surveillance on guard*," Oncoimmunology. 2014 Aug. 3; 3(8): e952201.<br>Tang et al., "*Apoptosis and anergy of T cell induced by pancreatic stellate cells-derived galectin-1 in pancreatic cancer*," Tumour Biol. 2015 Mar. 1. [Epub ahead of print].<br>Wu et al., "*Galectin-1 dysregulation independently predicts disease specific survival in bladder urothelial carcinoma*," J Urol. 2015 March; 193(3): 1002-8. doi: 10.1016/j.juro.2014.09.107. Epub 2014 Oct. 2.<br>Martinez-Bosch et al., "*Galectin-1 drives pancreatic carcinogenesis through stroma remodeling and Hedgehog signaling activation*," Cancer Res. 2014 Jul. 1; 74(13): 3512-24. doi: 10.1158/0008-5472.CAN-13-3013. Epub 2014 May 8.<br>Dalotto-Moreno et al., "*Targeting galectin-1 overcomes breast cancer-associated immunosuppression and prevents metastatic disease*," Cancer Res. 2013 Feb. 1; 73(3): 1107-17. doi: 10.1158/0008-5472.CAN-12-2418. Epub 2012 Nov. 29. |
| | | Heart disease | Al-Salam et al., "*Galectin-1 in early acute myocardial infarction*," PLoS One. 2014 Jan. 31; 9(1): e86994. doi: 10.1371/journal.pone.0086994. eCollection 2014.<br>Seropian et al., "*Galectin-1 controls cardiac inflammation and ventricular remodeling during acute myocardial infarction*," Am J Pathol. 2013 January; 182(1): 29-40. doi: 10.1016/j.ajpath.2012.09.022. Epub 2012 Nov. 9. |
| | | HIV-1 | St-Pierre et al., "*Galectin-1-specific inhibitors as a new class of compounds to treat HIV-1 infection*," Antimicrob Agents Chemother. 2012 January; 56(1): 154-62. doi: 10.1128/AAC.05595-11. Epub 2011 Nov. 7.<br>Sato et al., "*Glycans, galectins, and HIV-1 infection*," Ann NY Acad Sci. 2012 April; 1253: 133-48. doi: 10.1111/j.1749-6632.2012.06475.x.<br>Mercier et al., "*Galectin-1 promotes HIV-1 infectivity in macrophages through stabilization of viral adsorption*," Virology. 2008 Feb. 5; 371(1): 121-9. Epub 2007 Oct. 29. |

TABLE 1-continued

Summary Table of Protein Targets and their Associated Diseases

| Protein X | Accession Number (Homo sapiens) | Disease Y | Exemplified References |
|---|---|---|---|
| Uridine phosphorylase 2 | NP_001128570.1 (for isoform b) | Cancer; colon cancer | Ashour et al., "Effect of administration of 5-(phenylselenenyl)acyclouridine, an inhibitor of uridine phosphorylase, on the anti-tumor efficacy of 5-fluoro-2'-deoxyuridine against murine colon tumor C26-10," Biochem Pharmacol. 2000 Sep. 1; 60(5): 687-92.<br>Liu et al., "Expression, characterization, and detection of human uridine phosphorylase and identification of variant uridine phosphorolytic activity in selected human tumors," Cancer Res. 1998 Dec. 1; 58(23); 5418-24.<br>Pizzorno et al., "Phase I clinical and pharmacological studies of benzylacyclouridine, a uridine phosphorylase inhibitor," Clin Cancer Res. 1998 May; 4(5): 1165-75. |
| Estrogen receptor beta | AAC05985 | Cancer; prostate cancer; breast cancer | Dey et al., "Estrogen Receptor β2 Induces Hypoxia Signature of Gene Expression by Stabilizing HIF-1α in Prostate Cancer," PLoS One. 2015 May 26; 10(5): e0128239. doi: 10.1371/journal.pone.0128239. eCollection 2015.<br>Hamilton et al., "Biologic Roles of Estrogen Receptor-β and Insulin-Like Growth Factor-2 in Triple-Negative Breast Cancer," Biomed Res Int. 2015; 2015: 925703. doi: 10.1155/2015/925703. Epub 2015 Mar. 22.<br>Gallo et al., "Estrogen receptor beta in cancer: an attractive target for therapy," Curr Pharm Des. 2012; 18(19): 2734-57. |
| Caspase-6 | AAH04460.1 | Alzheimer's Disease | LeBlanc. "Caspase-6 as a novel early target in the treatment of Alzheimer's disease," Eur J Neurosci. 2013 June; 37(12): 2005-18. doi: 10.1111/ejn.12250.<br>Ramcharitar et al., "Cerebrospinal fluid tau cleaved by caspase-6 reflects brain levels and cognition in aging and Alzheimer disease," J Neuropathol Exp Neurol. 2013 September; 72(9): 824-32. doi: 10.1097/NEN.0b013e3182a0a39f.<br>Albrecht et al., "Caspase-6 activation in familial alzheimer disease brains carrying amyloid precursor protein or presenilin i or presenilin II mutations," J Neuropathol Exp Neurol. 2009 December; 68(12): 1282-93. doi: 10.1097/NEN.0b013e3181c1da10.<br>Horowitz et al., "Early N-terminal changes and caspase-6 cleavage of tau in Alzheimer's disease," J Neurosci. 2004 Sep. 8; 24(36): 7895-902. |
| Caspase-3 | CAC88866.1 | Parkinson's Disease | Hartmann et al., "Caspase-3: A vulnerability factor and final effector in apoptotic death of dopaminergic neurons in Parkinson's disease," Proc Natl Acad Sci USA. 2000 Mar. 14; 97(6): 2875-80.<br>Zawada et al., "Loss of angiotensin II receptor expression in dopamine neurons in Parkinson's disease correlates with pathological progression and is accompanied by increases in Nox4- and 8-OH guanosine-related nucleic acid oxidation and caspase-3 activation," Acta Neuropathol Commun. 2015 Feb. 3; 3: 9. doi: 10.1186/s40478-015-0189-z.<br>Tatton et al., "Apoptosis in Parkinson's disease: signals for neuronal degradation," Ann Neurol. 2003; 53 Suppl 3: S61-70; discussion S70-2.<br>Tatton et al., "Increased caspase 3 and Bax immunoreactivity accompany nuclear GAPDH translocation and neuronal apoptosis in Parkinson's disease," Exp Neurol. 2000 November; 166(1): 29-43. |
| | | Cancer; breast cancer | O'Donovan et al., "Caspase-3 in breast cancer," Clin Cancer Res. 2003 February; 9(2): 738-42.<br>Devarajan et al., "Down-regulation of caspase 3 in breast cancer: a possible mechanism for chemoresistance," Oncogene. 2002 Dec. 12; 21(57): 8843-51. |
| | | Alzheimer's Disease | D'Amelio et al., "Caspase-3 triggers early synaptic dysfunction in a mouse model of Alzheimer's disease," Nature Neuroscience 14, 69-76 (2011). Doi: 10.1038/nn.2709. |
| S100beta | NP_006263 | Alzheimer's Disease | Griffin et al., "Life-long overexpression of S100beta in Down's syndrome: implications for Alzheimer pathogenesis. Neurobiol Aging. 1998 Sepember-October; 19(5): 401-5.<br>Lambert et al., "Evidence for the association of the S100beta gene with low cognitive performance and dementia in the elderly," Mol Psychiatry. 2007 September; 12(9): 870-80. Epub 2007 Mar. 6.<br>Yu et al., "S100beta interaction with tau is promoted by zinc and inhibited by hyperphosphorylation in Alzheimer's disease," J Neurosci. 2001 Apr. 1; 21(7): 2240-6.<br>Cirillo et al., "S100B inhibitor pentamidine attenuates reactive gliosis and reduces neuronal loss in a mouse model of Alzheimer's disease," BioMed Research International, Article ID 508342. |

TABLE 1-continued

Summary Table of Protein Targets and their Associated Diseases

| Protein X | Accession Number (*Homo sapiens*) | Disease Y | Exemplified References |
|---|---|---|---|
| | | Down Syndrome | Griffin et al., "*Life-long overexpression of s100beta in Down's syndrome: implications for Alzheimer pathogenesis*," Neurobiol Aging. 1998 September-October; 19(5): 401-5. Gerlai et al., "*Abnormal exploratory behavior in transgenic mice carrying multiple copies of the human gene for S100 beta*," J Psychiatr Neurosci. 1995 March; 20(2): 105-12. Royston et al., "*Overexpression of S100beta in Down's syndrome: correlation with patient age and with beta-amyloid deposition*," Neuropathol Appl Neurobiol. 1999 October; 25(5): 387-93. |
| Phospholipase A2 | AAF09020 | Alzheimer's Disease | Sanchez-Mejia et al., "*Phospholipase A2 and arachidonic acid in Alzheimer's disease*," Biochim Biophys Acta. 2010 August; 1801(8): 784-90. doi: 10.1016/j.bbalip.2010.05.013. Epub 2010 May 27. Stephenson et al., "*Cytosolic phospholipase A2 (cPLA2) immunoreactivity is elevated in Alzheimer's disease brain*," Neurobiol Dis. 1996 February; 3(1): 51-63. Fonteh et al., "*Alterations in cerebrospinal fluid glycerophospholipids and phospholipase A2 activity in Alzheimer's disease*," J Lipid Res. 2013 October; 54(10): 2884-97. doi: 10.1194/jlr.M037622. Epub 2013 Jul. 18. Sanchez-Mejia et al., "*Phospholipase A2 reduction ameliorates cognitive deficits in a mouse model of Alzheimer's disease*," Nature Neuroscience 11, 1311-1318 (2008) Published online: 19 Oct. 2008. doi: 10.1038/nn.2213. |
| | | Epilepsy | Farooqui et al., "*Inhibitors of brain phospholipase A2 activity: their neuropharmacological effects and therapeutic importance for the treatment of neurologic disorders*," Pharmacol Rev. 2006 September; 58(3): 591-620. Gattaz et al., "*Increased PLA2 activity in the hippocampus of patients with temporal lobe epilepsy and psychosis*," J Psychiatr Res. 2011 December; 45(12): 1617-20. doi: 10.1016/j.jpsychires.2011.07.005. Epub 2011 Aug. 3. |
| | | Schizophrenia | Law et al., "*The role of phospholipases A2 in schizophrenia*," Mol Psychiatry. 2006 June; 11(6): 547-56. Gattaz et al., "*Phospholipase A2 activity and the hypofrontality of schizophrenia, Prostaglandins*," Leukot Essent Fatty Acids, 1996 August; 55(1-2): 109-13. Smesny et al., "*Phospholipase A2 activity is associated with structural brain changes in schizophrenia*," Neuroimage. 2010 Oct. 1; 52(4): 1314-27. doi: 10.1016/j.neuroimage.2010.05.009. Epub 2010 May 18. |
| Hematopoietic prostaglandin D synthase | AAK07679.1 | Duchenne muscular dystrophy (DMD) | Kamauchi et al., "*Hematopoietic prostaglandin D synthase inhibitors for the treatment of duchenne muscular dystrophy*," Brain Nerve. 2011 November; 63(11): 1261-9. Okinaga et al., "*Induction of hematopoietic prostaglandin D synthase in hyalinated necrotic muscle fibers: its implication in grouped necrosis*," Acta Neuropathol. 2002 October; 104(4): 377-84. Epub 2002 Jun. 6. |
| | | Alzheimer's Disease | Mohri et al., "*Hematopoietic prostaglandin D synthase and DP1 receptor are selectively upregulated in microglia and astrocytes within senile plaques from human patients and in a mouse model of Alzheimer disease*," J Neuropathol Exp Neurol. 2007 June; 66(6): 469-80. |
| Glutathione S-transferase | AAC51280.1 | Cancer; CML; lung cancer | Kassogue et al., "*Association of glutathione S-transferase (GSTM1 and GSTT1) genes with chronic myeloid leukemia*," Springerplus. 2015 May 1; 4: 210. doi: 10.1186/s40064-015-0966-y. eCollection 2015. Houlston, "*Glutathione S-Transferase M1 Status and Lung Cancer Risk*," Cancer Epidemiol Biomarkers Prev August 1999 8; 675. Townsend et al., "*The role of glutathione-S-transferase in anti-cancer drug resistance*," Oncogene (2003) 22, 7369-7375. doi: 10.1038/sj.onc.1206940. |
| | | Parkinson's Disease | Shi et al., "*Identification of glutathione S-transferase Pi as a protein involved in Parkinson disease progression*," Am J Pathol. 2009 July; 175(1): 54-65. Wang et al., "*Association between Glutathione S-transferase M1/Glutathione S-transferase T1 polymorphisms and Parkinson's disease: a meta-analysis*," J Neurol Sci. 2014 Mar. 15; 338(1-2): 65-70. doi: 10.1016/j.jns.2013.12.018. Epub 2013 Dec. 17. |
| | | Alzheimer's Disease | Lovell et al., "*Decreased glutathione transferase activity in brain and ventricular fluid in Alzheimer's disease*," Neurology. 1998 December; 51(6): 1562-6. |

TABLE 1-continued

Summary Table of Protein Targets and their Associated Diseases

| Protein X | Accession Number (Homo sapiens) | Disease Y | Exemplified References |
|---|---|---|---|
| 11-beta-hydroxysteroid dehydrogenase | AAC31757 | Metabolic Disorder | Spalletta et al., "Glutathione S-transferase P1 and T1 gene polymorphisms predict longitudinal course and age at onset of Alzheimer disease," Am J Geriatr Psychiatry. 2007 October; 15(10): 879-87. Yoon et al., "Discovery of pyridyl sulfonamide 11-beta-hydroxysteroid dehydrogenase type 1 (11β-HSD1) inhibitors for the treatment of metabolic disorders," Bioorg Med Chem Lett. 2014 Nov. 1; 24(21): 5045-9. doi: 10.1016/j.bmcl.2014.09.012. Epub 2014 Sep. 16. Anil et al., "A novel 11β-hydroxysteroid dehydrogenase type1 inhibitor CNX-010-49 improves hyperglycemia, lipid profile and reduces body weight in diet induced obese C57B6/J mice with a potential to provide cardio protective benefits," BMC Pharmacol Toxicol. 2014 Aug. 7; 15: 43. doi: 10.1186/2050-6511-15-43. Ratziu. "Targeting non-alcoholic fatty liver disease through 11-βHSD1 inhibition," Lancet Diabetes Endocrinol. 2014 May; 2(5): 354-6. doi: 10.1016/s2213-8587(14)70028-2. Epub 2014 Feb. 17. Wamil et al., "Inhibition of 11 beta-hydroxysteroid dehydrogenase type 1 as a promising therapeutic target," Drug Discovery Today. 2007 July; 12(13-14): 504-20. Epub 2007 Jun. 27. |
| | | Cancer; colon cancer; osteosarcoma | Moravec et al., "Expression of 11β-hydroxysteroid dehydrogenase type 2 is deregulated in colon carcinoma," Histol Histopathol. 2014 April; 29(4): 489-96. Epub 2013 Nov. 5. Jiang et al., "Epithelial-specific deletion of 11β-HSD2 hinders Apcmin/+ mouse tumorigenesis," Mol Cancer Res. 2013 September; 11(9): 1040-50. doi: 10.1158/1541-7786.MCR-13-0084-T. Epub 2013 Jun. 5. Patel et al., "Expression of 11β-hydroxysteroid dehydrogenase enzymes in human osteosarcoma: potential role in pathogenesis and as targets for treatments," Endocr Relat Cancer. 2012 Jul. 22; 19(4): 589-98. doi: 10.1530/ERC-12-0079. Print 2012 August. |
| Adenosine 5'-phosphosulfate reductase (Mycobacterium tuberculosis) | NP_216908 | Tuberculosis | Cosconati et al., "Structure-based virtual screening and biological evaluation of Mycobacterium tuberculosis adenosine 5'-phosphosulfate reductase inhibitors," J Med Chem. 2008 Nov. 13; 51(21): 6627-30. doi: 10.1021/jm800571m. Epub 2008 Oct. 15. Paritala et al., "A continuous spectrophotometric assay for adenosine 5'-phosphosulfate reductase activity with sulfite-selective probes," Anal Biochem. 2013 Sep. 1; 440(1): 32-9. doi: 10.1016/j.ab.2013.05.007. Epub 2013 May 24. Paritala et al., "Design, synthesis and evaluation of Fe—S targeted adenosine 5'-phosphosulfate reductase inhibitors," Nucleosides Nucleotides Nucleic Acids. 2015; 34(3): 199-220. doi: 10.1080/15257770.2014.978012. |

For example, as described below, stabilized analogues of Cu/Zn-SOD1 or DJ-1 can be used to treat ALS, Parkinson's and/or Alzheimer's Disease.

SOD1 and Amyotrophic Lateral Sclerosis (ALS)

Amyotrophic lateral sclerosis is a progressive neurodegenerative disease caused by death of motor neurons in the brain and spinal cord. The overall median survival from onset of symptoms ranges between 2-3 years for cases with bulbar onset to 3-5 years for cases with limb onset. Lifetime risk of ALS is 1/400 to 1/1000 with a median annual incidence of 1.89 and a median prevalence of 5.2 per 100,000 each year. There exists no cure for ALS and the only FDA-approved treatment for ALS, riluzole (Rilutek), prolongs median survival by a mere 2-3 months when taken for an eighteen month duration. Thus, novel therapeutic strategies for ALS continue to be crucial. Approximately ten percent of ALS is familial (fALS) and approximately twenty percent of fALS cases are caused by autosomal dominant mutations in the ubiquitously expressed protein SOD1. Over 100 SOD1 mutations have been identified which are linked with fALS and it is thought they confer a toxic gain of function. As the clinical phenotypes of patients with various fALS SOD1-associated mutations are more alike than different, and all appear to cause the death of motor neurons, it has been hypothesized that mutations share common properties and mechanisms of cytotoxicity. In addition to causing twenty percent of fALS, SOD1 may be playing a role in sporadic ALS. Evidence is emerging that a subset of sporadic ALS is characterized by unfolded WT SOD1, and that oxidatively modified SOD1 slows axonal transport to a similar extent to the G93A SOD1 variant. Numerous other reports have also implicated oxidized/misfolded WT SOD1 as being cytotoxic and/or related to sporadic ALS.

One prevailing hypothesis for the mechanism of the toxicity of ALS-associated SOD1 variants involves dimer destabilization and dissociation into monomers, which then nucleate the formation of higher-order aggregates. ALS-associated variants of SOD1, such as G85R, are found as monomers in ALS patients and a number of modifications, including loss of Cu or Zn, cleavage of the native, intramolecular disulfide, oxidation, glutathionylation, and fALS-associated mutation, predispose the SOD1 dimer to dissociate. X-ray crystal structures of both A4V, and to a lesser extent I113T, yeast two-hybrid analysis of H46R, A4V, and H48Q, dissociation of G85R, G93R, E100G, and I113T by chaotrophs, and molecular dynamics simulations are all consistent with this hypothesis; mutations and modifications destabilize dimer formation.

SOD1 dimers contain two cysteine residues at the dimer interface whose sulfhydryl groups are approximately nine angstroms apart. These sulfhydryl groups can be targeted by maleimide cross-linkers which lead to strong stabilization of ALS-associated SOD1 dimers. Surprisingly, while cross-linking at sulfhydryl groups by the maleimides occurred by predicted maleimide-mediated mechanisms, for the maleimide dithio-bismaleimidoethane (DTME), it was found that stabilization of the SOD1 dimer possibly occurred through both maleimide interaction with the sulfhydryl group of Cys111 on one SOD1 monomer as well as thiol-disulfide exchange between the disulfide spacer of DTME and the sulfhydryl group of the Cys111 on the second SOD1 monomer. Unfortunately, maleimides are highly irritating locally and have an $LD_{50}$ in mice of 9 mg/kg with renal, hepatic, neurologic and hematologic toxicities as the principal effects of the drug in this species. Therefore, in certain embodiments, the invention relates to the discovery of molecules that can cross-link SOD1 dimers in order to fully assess small molecule-mediated covalent dimer formation of SOD1 as a therapeutic strategy for ALS.

DJ-1 and Parkinson's Disease (PD)

The progressive neurodegenerative disorder PD is characterized by the loss of dopaminergic neurons in the substania nigra *pars compacta* and α-synuclein-rich protein deposits known as Lewy bodies. A variety of pharmacological treatment options exist for the early-stage symptoms of PD as the patient becomes functionally impaired. However, as the disease progresses, all of these agents, which primarily treat the symptoms of PD, become ineffective as fewer dopaminergic neurons survive. Thus, as the ability to slow the progression of the disease remains elusive, novel directions in therapeutic development are necessary to further combat PD.

While the majority (>90%) of PD cases are idiopathic, mutations in PARK7, encoding the 189-amino acid homodimeric protein DJ-1, are known to be a rare cause of autosomal recessive early-onset Parkinson disease. Some evidence also indicates polymorphisms in PARK7 confer risk in sporadic PD patients. Biochemical and cell culture analysis of PD-linked variants of DJ-1 suggest a number of mechanisms through which structural defects, including loss of stability and dimer formation, may lead to a loss-of-function that is associated with PD pathogenicity, such as reduced ability to prevent α-synuclein aggregation, deficiency in oxidative stress-dependent RNA-binding activity, reduced ability to act as a neuroprotective transcriptional co-activator, and increased sensitivity to oxidative stress-induced cell death related to mitochondrial defects. In additional to recessive PD-related mutants of DJ-1 being implicated in disease, analysis of DJ-1 in the frontal cortex of patients with sporadic PD and Alzheimer's disease reveal that acidic isoforms of monomeric DJ-1 and basic isoforms of SDS-resistant dimeric DJ-1 selectively accumulate in these diseases, with DJ-1 irreversibly oxidized by carbonylation as well as by methionine oxidation to methionine sulfone. Over-oxidation of DJ-1 has been found to produce structural destabilization similar to PD-related mutations, suggesting that dysfunctional DJ-1 due to aberrant modifications could be a cause of sporadic neurodegenerative cases.

Just as loss of DJ-1 function appears to contribute to the etiology of PD, evidence suggests that enhancement of DJ-1 function could compensate for other causes of PD. DJ-1 protects against degeneration of nigral dopaminergic neurons in PD rat models involving both 6-hydroxydopamine and rotenone treatment. Viral-mediated DJ-1 overexpression in the MPTP mouse model has also proved efficacious in reducing nigral dopamine neuron loss. Likewise, pharmacological upregulation of DJ-1 with the histone deacetylase inhibitor phenylbutyrate rescues cells from oxidative stress and mutant α-synuclein toxicity, as well as protects dopaminergic neurons from MPTP-induced neurotoxicity and prevents age-related motor and cognitive decline in mice with diffuse Lewy body disease. Thus, enhancement of DJ-1 activity could serve as a therapeutic strategy in a possibly wide variety of PD cases. Previously, in silico methods have been used to identify potential small molecule binding sites on DJ-1 and for identifying small molecules capable of interacting with DJ-1 and modulating its oxidation state that have neuroprotective effects in vivo. However, Cys53s in DJ-1 are more closely spaced than Cys111s in SOD1, hindering previous attempts to covalently dimerize DJ-1 using maleimide crosslinkers.

Dithiols and Cyclic Disulfides as Covalent Dimerizers and Therapeutics

The cyclic disulfides described herein can covalently dimerize any one of the Protein X listed in Table 1 through their respective closely spaced dimer interface cysteines. Theoretically, a cyclic disulfide could undergo thiol-disulfide exchange with the cysteine of a Protein X, leaving a free thiolate to react with the remaining monomer (FIG. 1). Dithiols might also be capable of forming covalent dimers if the thiol groups are properly spaced and appropriately reactive. In agreement with this hypothesis, we present several cyclic disulfides and a dithiol discovered in preliminary screens that are capable of covalently dimerizing any one of the Protein X listed in Table 1.

Representative Methods of the Invention

In certain embodiments, the invention relates to a method comprising the step of contacting a compound of Formula I or a compound of Formula II with a first Protein X and a second Protein X under conditions suitable for cross-linking the first Protein X to the second Protein X, thereby cross-linking the first Protein X to the second Protein X, wherein the first Protein X comprises a first cysteine residue; the second Protein X comprises a second cysteine residue; the compound of Formula I is

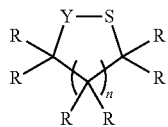

I wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and the compound of Formula II is

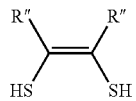

II

Wherein R" is —H, alkyl, or aryl, or both R", taken together, form a ring; wherein any alkyl, aryl, or ring may be substituted with —OH, alkyl, or halo and wherein Protein X is selected from Table 1.

In certain embodiments, the invention relates to a method comprising the step of contacting a compound with a first Protein X and a second Protein X under conditions suitable for cross-linking the first Protein X to the second Protein X, thereby cross-linking the first Protein X to the second Protein X, wherein the first Protein X and the second Protein X are at least 80%, 85%, 86%, 87%, 88%, 89%, 90%, 91%, 92%, 93%, 94%, 95%, 96%, 97%, 98%, 99%, or 100% identical or homologous to one another and wherein the first Protein X and the second Protein X are any one of the Protein X listed in Table 1; and the compound is a compound of Formula I

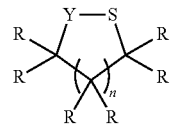

I

Wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl.

In certain embodiments, the invention relates to any one of the aforementioned methods, wherein Y is S.

In certain embodiments, the invention relates to any one of the aforementioned methods, wherein Y is S=O.

In certain embodiments, the invention relates to any one of the aforementioned methods, wherein Y is S(=O)$_2$.

In certain embodiments, the invention relates to any one of the aforementioned methods, wherein n is 1 or 2.

In certain embodiments, the invention relates to any one of the aforementioned methods, wherein n is 1.

In certain embodiments, the invention relates to any one of the aforementioned methods, wherein n is 2.

In certain embodiments, the invention relates to any one of the aforementioned methods, wherein the compound is selected from the group consisting of

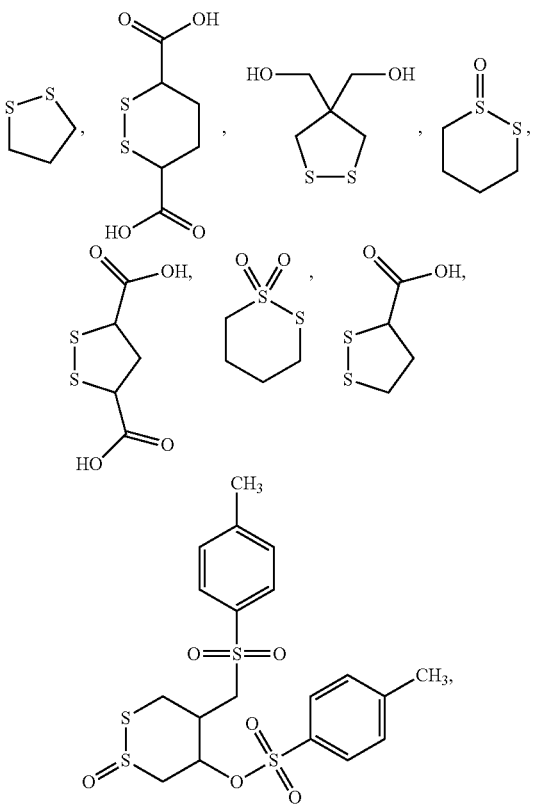

-continued

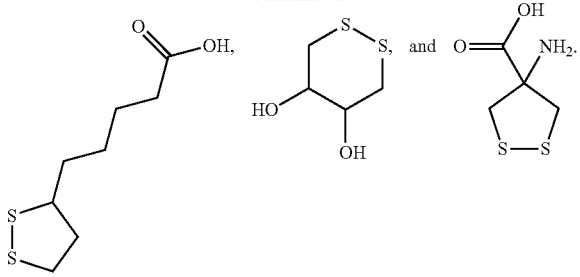

In certain embodiments, the invention relates to a method comprising the step of contacting a compound disclosed herein with a first Protein X and a second Protein X under conditions suitable for cross-linking the first Protein X to the second Protein X, thereby cross-linking the first Protein X to the second Protein X, wherein the first Protein X and the second Protein X are at least 80%, 85%, 86%, 87%, 88%, 89%, 90%, 91%, 92%, 93%, 94%, 95%, 96%, 97%, 98%, 99%, or 100% homologous or identical to one another; the first Protein X and the second Protein X are any one of the Protein X listed in Table 1; and the compound is a compound of Formula II

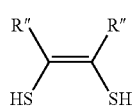

II

Wherein R" is —H, alkyl, or aryl, or both R", taken together, form a ring; wherein any alkyl, aryl, or ring may be substituted with —OH, alkyl, or halo.

In certain embodiments, the invention relates to any one of the aforementioned methods, wherein the R" form a six-membered ring. In certain embodiments, the invention relates to any one of the aforementioned methods, wherein the R" form an aromatic ring. In certain embodiments, the invention relates to any one of the aforementioned methods, wherein the R" form a six-membered aromatic ring.

In certain embodiments, the invention relates to any one of the aforementioned methods, wherein the compound is

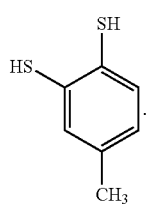

In certain embodiments, the invention relates to any one of the aforementioned methods, wherein the first Protein X and the second Protein X have at least 95% sequence homology or identity to one another.

In certain embodiments, the invention relates to any one of the aforementioned methods, wherein the first Protein X and the second Protein X have at least 98% sequence homology or identity to one another.

In certain embodiments, the invention relates to any one of the aforementioned methods, wherein the first Protein X and the second Protein X have at least 99% sequence homology or identity to one another.

In certain embodiments, the invention relates to any one of the aforementioned methods, wherein the first Protein X and the second Protein X are wild type of any one of the Protein X listed in Table 1.

In certain embodiments, the invention relates to any one of the aforementioned methods, wherein the method is performed in vitro. For example, the cross-linking of the first and second Protein X with a compound of Formula I or Formula II occurs outside of a patient and then the resultant cross-linked, stabilized analogue of Formula III or Formula IV is administered to the patient in a therapeutically effective amount, such as for example, for enzyme replacement therapy. Alternatively, the cross-linking of the first and the second Protein X can occur in vivo. In this situation, the molecule represented by Formula I or Formula II is administered to a patient in a therapeutically effective amount to cross-link the first and second Protein X in the patient. In further embodiments, the invention relates to any one of the aforementioned methods, wherein the first Protein X and the second Protein X are cross-linked within a cell.

In certain embodiments, the invention relates to any one of the aforementioned methods, wherein the method is a method of inhibiting the activity of the first Protein X or the second Protein X.

In certain embodiments, the invention relates to any one of the aforementioned methods, wherein the method is a method of increasing the activity of the first Protein X or a second Protein X.

In certain embodiments, the invention relates to any one of the aforementioned methods, wherein the method is a method of stabilizing the first Protein X or the second Protein X.

In certain embodiments, the invention relates to any one of the aforementioned methods, wherein the method is a method of destabilizing the first Protein X or the second Protein X.

In certain embodiments, the invention relates to a method of treating or preventing a Disease Y listed in Table 1 for each Protein X, comprising the step of administering to a subject in need thereof a therapeutically effective amount of a compound of Formula I or a compound of Formula II, wherein the compound of Formula I is

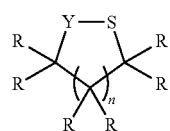

I

Wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and the compound of Formula II is

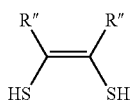

wherein R" is —H, alkyl, or aryl, or both R", taken together, form a ring; wherein any alkyl, aryl, or ring may be substituted with —OH, alkyl, or halo.

In certain embodiments, the invention relates to any one of the aforementioned methods, wherein the compound is a compound of Formula I; and Y is S.

In certain embodiments, the invention relates to any one of the aforementioned methods, wherein the compound is a compound of Formula I; and Y is S=O.

In certain embodiments, the invention relates to any one of the aforementioned methods, wherein the compound is a compound of Formula I; and Y is S(=O)$_2$.

In certain embodiments, the invention relates to any one of the aforementioned methods, wherein the compound is a compound of Formula I; and n is 1 or 2.

In certain embodiments, the invention relates to any one of the aforementioned methods, wherein the compound is a compound of Formula I; and n is 1.

In certain embodiments, the invention relates to any one of the aforementioned methods, wherein the compound is a compound of Formula I; and n is 2.

In certain embodiments, the invention relates to any one of the aforementioned methods, wherein the compound is a compound of Formula I; and the compound is selected from the group consisting of

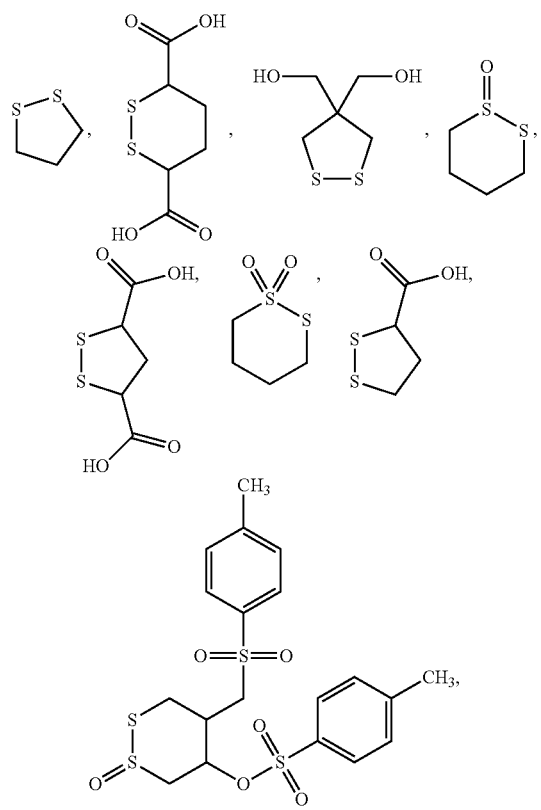

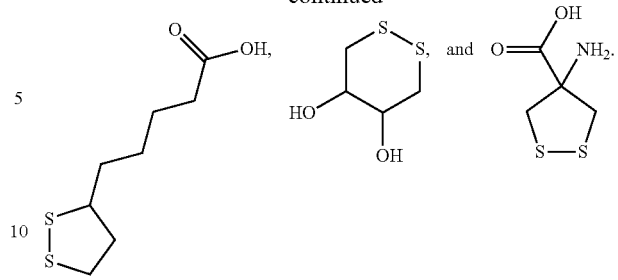

In certain embodiments, the invention relates to any one of the aforementioned methods, wherein the compound is a compound of Formula II; and the R" form a six-membered ring. In certain embodiments, the invention relates to any one of the aforementioned methods, wherein the compound is a compound of Formula II; and the R" form an aromatic ring. In certain embodiments, the invention relates to any one of the aforementioned methods, wherein the compound is a compound of Formula II; and the R" form a six-membered aromatic ring.

In certain embodiments, the invention relates to any one of the aforementioned methods, wherein the compound is a compound of Formula II; and the compound is

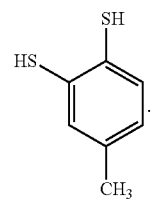

In certain embodiments, the invention relates to any one of the aforementioned methods, wherein a Disease Y is a neurodegenerative disease (such as, for example, Parkinson's Disease, ALS, Alzheimer's Disease, Huntington's Disease, Epilepsy, Frontotemporal Dementia, and/or DMD), cancer, autoimmune disease and/or Celiac disease, or any other Disease Y listed in Table 1.

Representative Compounds of the Invention

In certain embodiments, the invention relates to a compound of Formula I

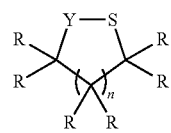

Wherein Y is S, S=O, or S(=O)$_2$; n is 0, 1, 2, 3, or 4; and R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl.

In certain embodiments, the invention relates to any one of the aforementioned compounds, wherein Y is S.

In certain embodiments, the invention relates to any one of the aforementioned compounds, wherein Y is S=O.

In certain embodiments, the invention relates to any one of the aforementioned compounds, wherein Y is S(=O)$_2$.

In certain embodiments, the invention relates to any one of the aforementioned compounds, wherein n is 1 or 2.

In certain embodiments, the invention relates to any one of the aforementioned compounds, wherein n is 1.

In certain embodiments, the invention relates to any one of the aforementioned compounds, wherein n is 2.

In certain embodiments, the invention relates to any one of the aforementioned compounds, wherein the proviso that the compound is not selected from the group consisting of

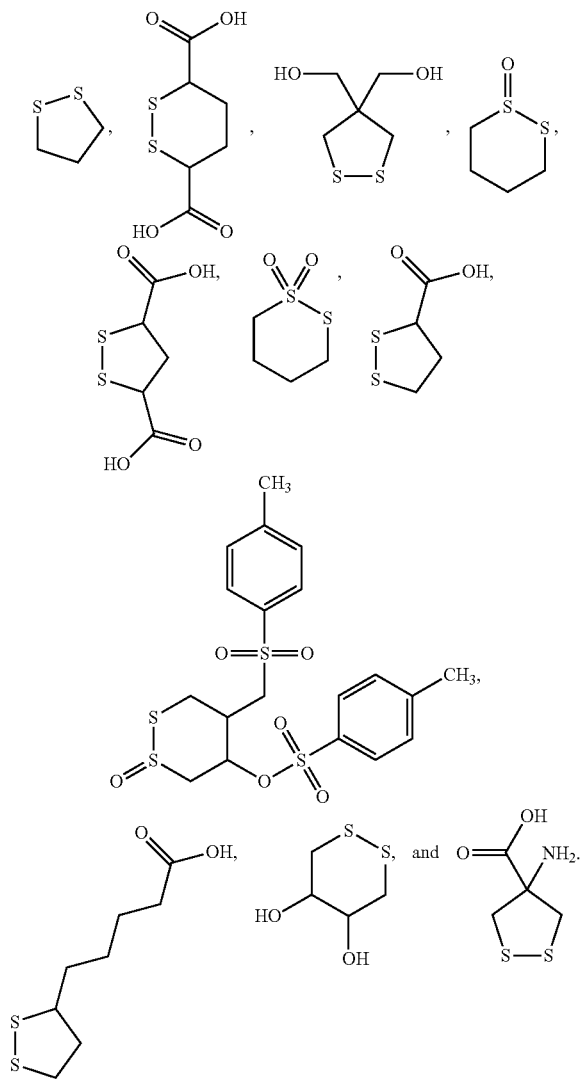

Representative Analogues of the Invention

One aspect of the invention is a stabilized analogue of any one of the Protein X listed in Table 1, wherein said analogue has a tertiary structure and comprises a first Protein X monomer and a second Protein X monomer; wherein the first Protein X monomer comprises a first cysteine residue; the second Protein X monomer comprises a second cysteine residue; the first cysteine residue is connected to the second cysteine residue by a connection; and the connection is a connection of Formula III or Formula IV:

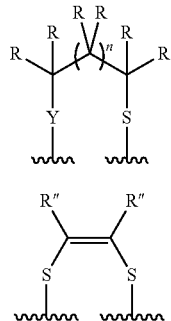

Wherein Y is S, S=O, or S(=O)$_2$; n is 0, 1, 2, 3, or 4; R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and R" is —H, alkyl, or aryl, or both R", taken together, form a ring; wherein any alkyl, aryl, or ring may be substituted with —OH, alkyl, or halo.

In certain embodiments, the present invention relates to any one of the aforementioned analogues, wherein the tertiary structure is substantially the same as the wild-type of any one of the Protein X listed in Table 1.

In certain embodiments, the present invention relates to any one of the aforementioned analogues, wherein the sequence homology or identity of the first Protein X monomer and the second Protein X monomer is greater than or equal to about 80%, 85%, 86%, 87%, 88%, 89%, 90%, 91%, 92%, 93%, 94%, 95%, 96%, 97%, 98%, 99%, or 100.

In certain embodiments, the present invention relates to any one of the aforementioned analogues, wherein the first Protein X monomer and the second Protein X monomer have substantially the same amino acid sequence.

In certain embodiments, the present invention relates to any one of the aforementioned analogues, wherein the first Protein X monomer of said analogue is the wild-type sequence or comprises one, two, three, four, five, six, seven, eight, nine, or ten point mutations as compared to the wild type sequence.

In certain embodiments, the present invention relates to any one of the aforementioned analogues, wherein the second Protein X monomer of said analogue is the wild-type sequence or comprises one, two, three, four, five, six, seven, eight, nine, or ten point mutations as compared to the wild type sequence.

In certain embodiments, the present invention relates to any one of the aforementioned analogues, wherein said analogue retains at least 80%, 85%, 86%, 87%, 88%, 89%, 90%, 91%, 92%, 93%, 94%, 95%, 96%, 97%, 98%, 99%, or 100% activity of the wild-type of any one of the Protein X listed in Table 1.

In certain embodiments, the present invention relates to any one of the aforementioned analogues, wherein said analogue retains at least 80%, 85%, 86%, 87%, 88%, 89%, 90%, 91%, 92%, 93%, 94%, 95%, 96%, 97%, 98%, 99%, or 100% activity of the wild-type of any one of the Protein X listed in Table 1 up to a temperature of about 75° C.

In certain embodiments, the present invention relates to any one of the aforementioned analogues, wherein said analogue is increased in stabilization from about 10° C. to about 60° C.

In certain embodiments, the present invention relates to any one of the aforementioned analogues, wherein said analogue is increased in stabilization from about 20° C. to about 40° C.

In certain embodiments, the present invention relates to any one of the aforementioned analogues, wherein said analogue is increased in stabilization from about 15° C. to about 25° C.

In certain embodiments, the present invention relates to any one of the aforementioned analogues, wherein said analogue is increased in stabilization from about 30° C. to about 50° C.

In certain embodiments, the present invention relates to any one of the aforementioned analogues, wherein said analogue is increased in stabilization about 20° C.

In certain embodiments, the present invention relates to any one of the aforementioned analogues, wherein said analogue is increased in stabilization about 40° C.

Definitions

The term "analogue" refers to a molecule substantially similar in function to any one of the Protein X listed in Table 1 or a fragment thereof.

The terms "percent (%) sequence similarity", "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

Specifically, the terms "percent (%) amino acid sequence identity" or "percent amino acid sequence homology" or "percent (%) identical" as used herein with respect to a reference polypeptide is defined as the percentage of amino acid residues in a candidate polypeptide sequence that are identical with the amino acid residues in the reference polypeptide sequence after aligning the sequences and introducing gaps, if necessary, to achieve the maximum percent sequence identity, without considering any conservative substitutions as part of the sequence identity. Alignment for the purpose of determining percent amino acid sequence identity can be achieved by various techniques known in the art, for instance, using publicly available computer software such as ALIGN or Megalign (DNASTAR). Those skilled in the art can determine appropriate parameters for measuring alignment, including any algorithms needed to achieve maximal alignment over the full length of the peptide sequence being used in the comparison. For example, in the context of the present invention, an analogue of SOD1 is said to share "substantial homology" with SOD1 if the amino acid sequence of said analogue is at least about 85%, at least about 90%, at least about 95%, or at least about 99% identical to wild-type.

To determine the percent identity and/or homology between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb.

Another non-limiting example of a mathematical algorithm utilized for the comparison of sequences is the algorithm of Myers and Miller, CABIOS 1988; 4: 1 1-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

Statistical analysis of the properties described herein may be carried out by standard tests, for example, t-tests, ANOVA, or Chi squared tests. Typically, statistical significance will be measured to a level of $p=0.05$ (5%), more preferably $p=0.01$, $p=0.001$, $p=0.0001$, $p=0.000001$.

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "preventing" is art-recognized, and when used in relation to Disease Y listed in Table 1 for each Protein X, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population. Prevention of a neurodegenerative disease or disorder, for example, includes the reduction and/or slowing down of the appearance of symptoms (e.g., a decrease in cognitive function) associated with the neurodegenerative disease or disorder as compared to subjects in a treated population versus an untreated control population A "therapeutically effective amount" of a compound, e.g., such as a polypeptide or peptide analogue of the present invention, with respect to use in treatment, refers to an amount of the polypeptide or peptide analogue of Formula I or Formula II described herein and/or the stabilized analogue of Formula III or Formula IV as described herein in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The terms "prophylactic" or "therapeutic" treatment are art-recognized and include administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

The term "patient" or "subject" as used herein in reference can encompasses veterinary uses, such as, for example, the testing of a rodent (e.g. a guinea pig, a hamster, a rat, a mouse), rabbit, murine (e.g. a mouse), canine (e.g. a dog), feline (e.g. a cat), equine (e.g. a horse), bovine (e.g., cow) a primate, simian (e.g. a monkey or ape), a monkey (e.g. marmoset, baboon), an ape (e.g. gorilla, chimpanzee, orangutan, gibbon). In preferred embodiments the patient is a human.

Other aspects and embodiments of the invention provide the aspects and embodiments described above with the term "comprising" replaced by the term "consisting of" and the aspects and embodiments described above with the term "comprising" replaced by the term "consisting essentially of".

"and/or" where used herein is to be taken as specific disclosure of each of the two specified features or components with or without the other. For example "A and/or B" is to be taken as specific disclosure of each (i) A, (ii) B and (iii) A and B, just as if each is set out individually.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

EXEMPLIFICATION

The invention now being generally described, it will be more readily understood by reference to the following examples which are included merely for purposes of illustration of certain aspects and embodiments of the present invention, and are not intended to limit the invention.

Example 1—General Materials and Methods

Cross-Linking and Western Blots

WtSOD1 or wtDJ-1 was incubated with 5-25 mM DTT for approximately 20 minutes and either buffer exchanged using Amicon Ultra-4 centrifugal spin concentrators (MWCo 10K) or using reversed phase chromatography (ZIPTIP, Millipore, Inc). Samples cleaned by ZIPTIPs were also subjected to incubation with 5 mM EDTA. SOD1 samples that were buffer exchanged using Amicon concentrators were exchanged into in HPLC water, whereas ZIPTIP samples were further exchanged after ZIPTIP into PBS, pH 7.4 or HPLC water. DTT-reduced SOD1 or DJ-1 was incubated at a 1:1 (20 µM:20 µM or 10 µM:10 µM) or 1:3 (20 µM:60 µM or 10 µM:30 µM) ratio of protein to cross-linker.

A variety of cross-linkers were used. Cross-linking was achieved by incubating the reaction in either PBS pH 7.4 or water at room temperature for 1 hour. After an hour the reactions were analyzed on a 15% SDS-PAGE gel with a non-cross-linked control, transferred to nitrocellulose membrane and western blotted using a polyclonal antibody to SOD1 or DJ-1. Repeated in triplicate.

In addition, DTME is a cleavable sulfhydryl-sulfhydryl cross-linking agent. Therefore, a cross-linking reaction containing 1:1 molar ratio of wtSOD1 or wtDJ-1 to DTME was performed at room temperature for one hour. After cross-linking, the reaction was split in half and half of the sample was run in a sample buffer containing DTT (reducing) and the other half in one containing no DTT (non-reducing). These samples along with non-cross-linked controls were then analyzed on a 15% SDS PAGE gel and western blotted as above.

Matrix Assisted Laser Desorption Ionization (MALDI)-Time of Flight (TOF)

wtSOD1 or wtDJ-1 was cross-linked as below. After cross-linking, 1 µL of sample was spotted on a MALDI target containing 1 µl of matrix, 20 mg/mL sinipic acid, and analyzed on a Bruker Daltonics Microflex. The MALDI was calibrated each time using a high molecular weight protein calibration standard, Protein Calibration Standard I (Bruker Daltonics). The MALDI-TOF was operated in linear mode using a laser power of between 72-90%. MALDI-TOF spectra were of cross-linked and non-cross-linked samples were analyzed using FlexAnalysis software (Bruker Daltonics). Repeated in triplicate.

Example 2

LC-MS Screen of Cyclic Disulfides with SOD1 Reveals Small Molecules that Covalently Link SOD1 Dimers.

Figure 2:
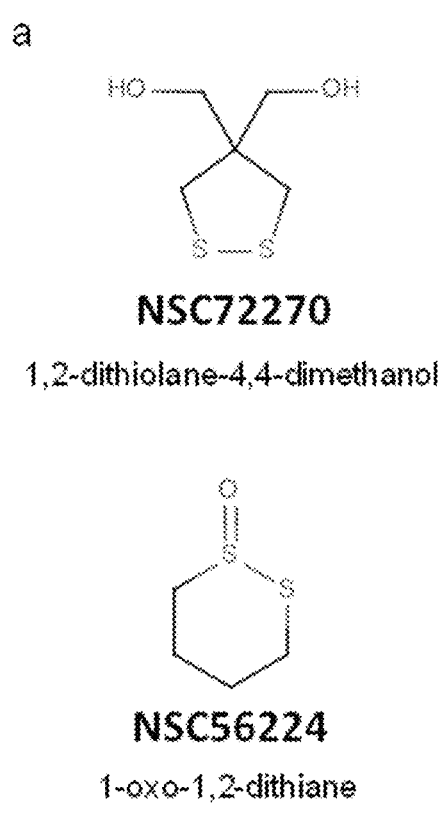
FIG. 2 depicts a preliminary LC-ESI-IonTrap-MS screen of cyclic disulfides that identifies multiple compounds that form covalent SOD1 dimers. a) Cyclic disulfides identified in our preliminary screen that form covalent-linked SOD1 dimers. b) Deconvoluted LC-MS spectra of SOD1 with no compound (top) and with 1-oxo-1,2-dithiane (bottom).
Figure 2:
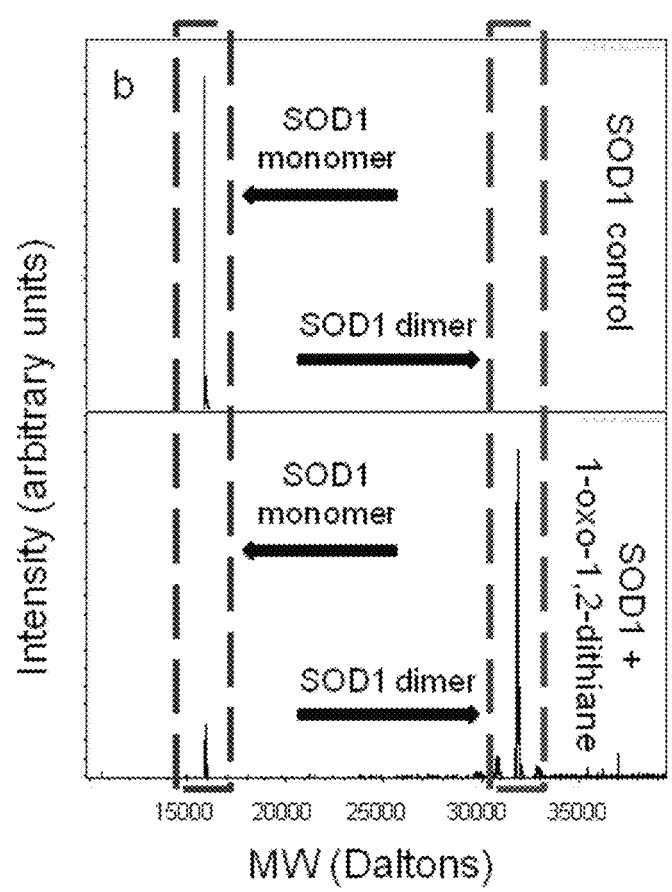
Figure 4:
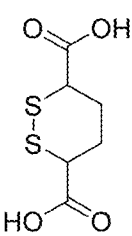
FIG. 4 depicts examples of cyclic disulfide compounds that are able to form covalent dimers of SOD1.
Figure 4:
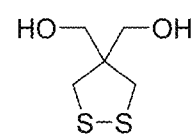
Figure 4:
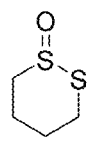
Figure 4:
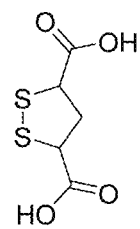
Figure 4:
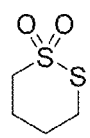
Figure 4:
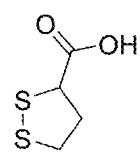
Figure 4:
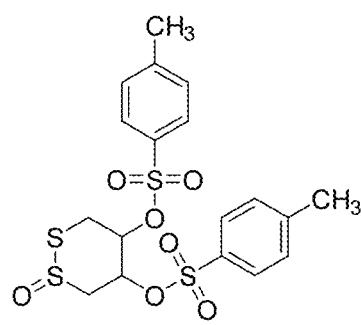
Figure 4:
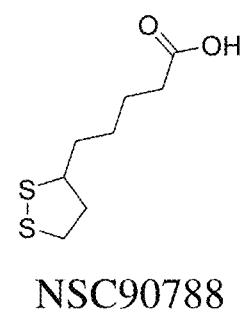
Figure 4:
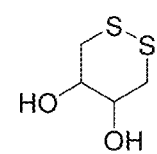
Figure 4:
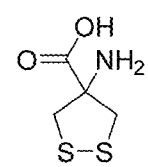
Figure 5:
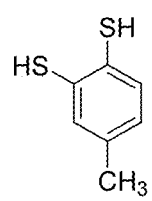
FIG. 5 depicts a dithiol that is able to form covalent dimers of SOD1.

Compounds being evaluated were dissolved and incubated with recombinant human WT SOD1. Reactions were analyzed by LC-ESI-IonTrap-MS on a HCT Ultra ion trap (Bruker Daltonics, Billerica, Mass., USA). The resulting data was examined using DataAnalysis 3.4 (Bruker Daltonics Inc., Billerica, Mass., USA). Mass spectra were averaged across the retention times corresponding to when SOD1 was found to be eluting and Maximum Entropy Deconvolution was applied to the resulting average mass spectrum in order to determine the molecular weight of the uncharged species detected. Significant dithiol- and cyclic disulfide-mediated covalent dimer formation has been observed with multiple different compounds. For example, the changes in mass of the covalently linked SOD1 dimers observed suggest both 1,2-dithiolane-4,4-dimethanol and 1-oxo-1,2-dithiane (FIG. 2a) are capable of covalently dimerizing SOD1. Of note, 1-oxo-1,2-dithiane was able to cross-link the majority of SOD1 monomers in the sample (FIG. 2b) and the mass of the cross-linked SOD1 dimer corresponds to the loss of one water molecule after the addition of 1-oxo-1,2-dithiane to a SOD1 dimer. 1-oxo-1,2-dithiane (NSC56224) and its analogues have been partially characterized previously for their ability to attack retroviral zinc fingers. Identified compounds can be found in FIG. 4 and FIG. 5.

Example 3

LC-MS Screen of Cyclic Disulfides with DJ-1 Reveals Molecules that Covalently Link DJ-1 Dimers.

Figure 3:
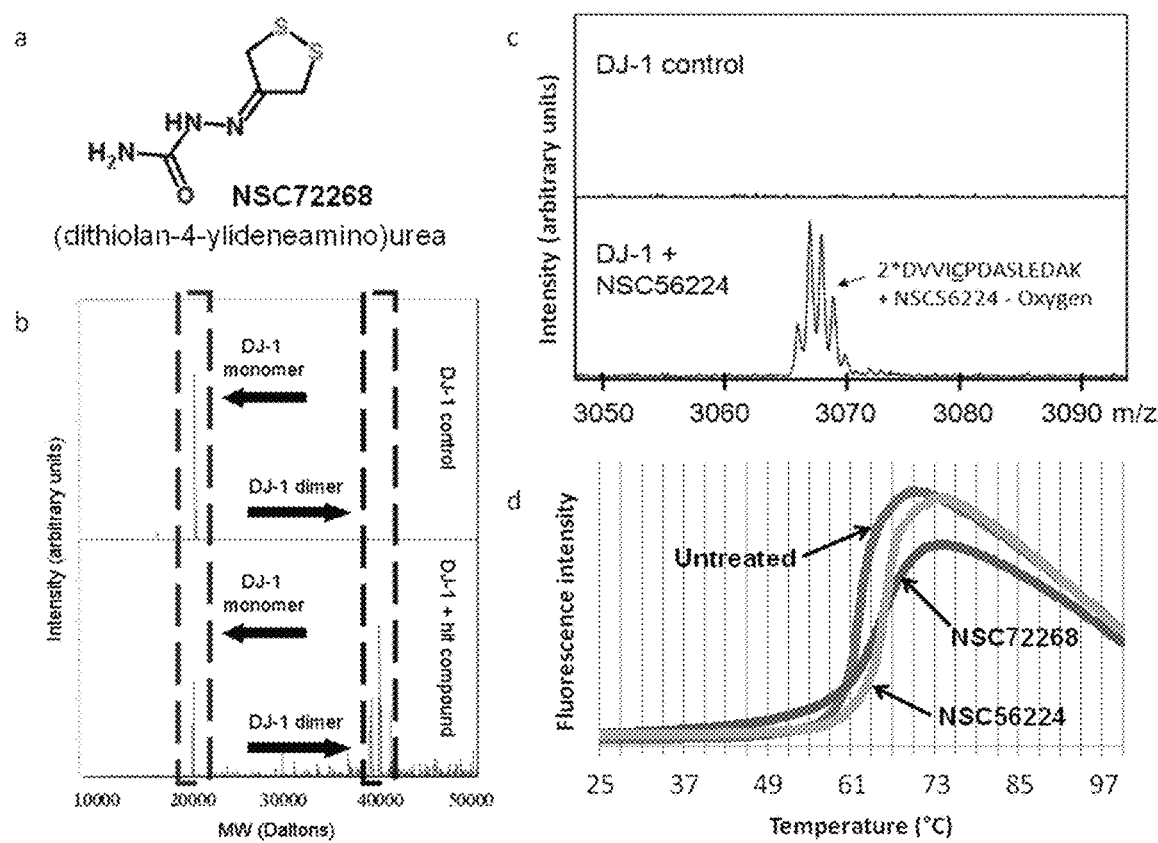
FIG. 3 depicts a preliminary LC-ESI-IonTrap-MS screen of cyclic disulfides that identifies compounds that form covalent DJ-1 dimers at Cys53 and increase the thermal stability of DJ-1. a) NSC72268 was identified as a specific covalent dimerizer of DJ-1. b) Deconvoluted spectra of untreated DJ-1 (top) and NSC72268-treated DJ-1. c) MALDI-TOF-MS spectra showing a detected ion specific for NSC56224-treated DJ-1 corresponding to two trypsin digest fragments of DJ-1 containing Cys53 (underlined) linked by NSC56224. d) NSC56224 and NSC72268 increase the measured denaturation temperature of DJ-1 relative to untreated DJ-1 (N=3, error bars not shown but standard deviation is less than thickness of lines).
Figure 6:
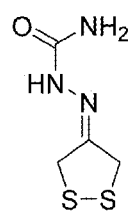
FIG. 6 depicts examples of cyclic disulfide compounds that are able to form covalent dimers of DJ-1.
Figure 6:
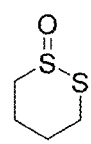

Using the same method as described for SOD1, compounds were screened against WT DJ-1. In addition to NSC56224 again being identified as a covalent dimerizer of DJ-1, NSC72268 was identified as a specific DJ-1 covalent dimerizer (FIG. 3a,b). Digesting NSC56224-linked DJ-1 with trypsin following by MALDI-TOF-MS confirmed NSC56224 covalently linked DJ-1 dimers at Cys53 (FIG. 3c). Both NSC56224 and NSC72268 were found to increase the denaturation temperature of DJ-1 measured with differential scanning fluorimetry (FIG. 3d) (Niesen et al., 2007), suggesting covalent dimerization increased DJ-1 thermal stability. NSC72268 and NSC56224 are shown in FIG. 6.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A stabilized analogue comprising a first Protein X and a second Protein X cross-linked to one another by a compound of Formula I or a compound of Formula II, wherein
the first Protein X comprises a first cysteine residue and has at least 80%, 85%, 86%, 87%, 88%, 89%, 90%, 91%, 92%, 93%, 94%, 95%, 96%, 97%, 98%, 99%, or 100% sequence identity to CAC88866.1;
the second Protein X comprises a second cysteine residue and has at least 80%, 85%, 86%, 87%, 88%, 89%, 90%, 91%, 92%, 93%, 94%, 95%, 96%, 97%, 98%, 99%, or 100% sequence identity to CAC88866.1;
the compound of Formula I is

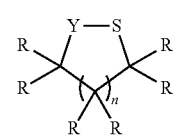

I wherein
Y is S, S=O, or S(=O)$_2$;
n is 0, 1, 2, 3, or 4; and

R is independently selected from the group consisting of —H, —OH, —NH₂, —NHR', —N(R')₂, alkyl, —OMs, —OTs, —OTf, and —CO₂H; or any two geminal R groups, taken together, form an imine; or any two vicinal R groups, taken together, form a ring;

wherein any alkyl or imine may be substituted with a carbamide, a carboxylate, or a hydroxyl; and R' is alkyl or aryl; and the compound of Formula II is

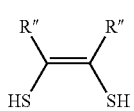

wherein

R" is —H, alkyl, or aryl, or both R", taken together, form a ring; wherein any alkyl, aryl, or ring may be substituted with —OH, alkyl, or halo.

2. The stabilized analogue of claim 1, wherein the first Protein X or the second Protein X is CAC88866.1.

3. The stabilized analogue of claim 1, wherein the first Protein X and the second Protein X are at least 80%, 85%, 86%, 87%, 88%, 89%, 90%, 91%, 92%, 93%, 94%, 95%, 96%, 97%, 98%, 99%, or 100% identical to one another.

4. The stabilized analogue of claim 1, wherein the compound is a compound of Formula I; and the compound is selected from the group consisting of

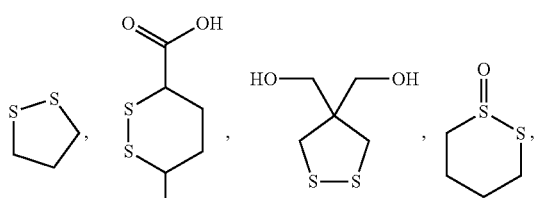

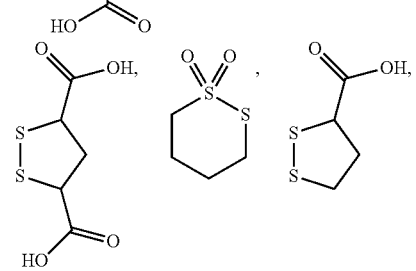

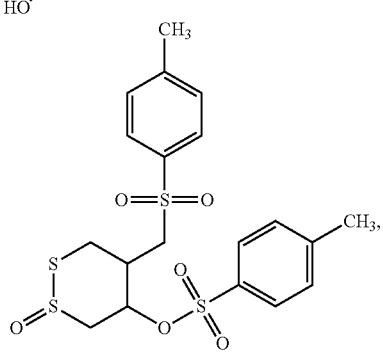

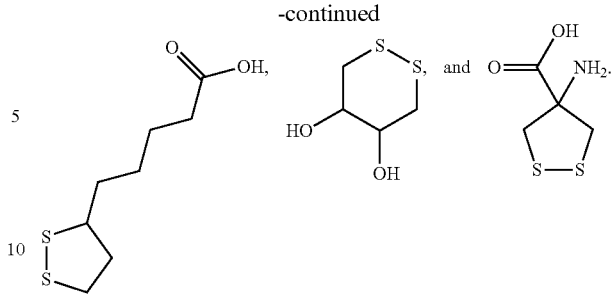

5. The stabilized analogue of claim 1, wherein the compound is a compound of Formula II, and the compound is

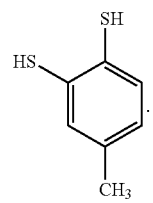

6. The stabilized analogue of claim 1, wherein the stabilized analogue is a compound of Formula III or Formula IV:

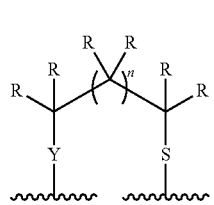

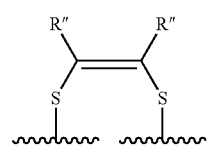

wherein

Y is S, S=O, or S(=O)₂;

n is 0, 1, 2, 3, or 4;

R is independently selected from the group consisting of —H, —OH, —NH₂, —NHR', —N(R')₂, alkyl, —OMs, —OTs, —OTf, and —CO₂H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and R" is —H, alkyl, or aryl, or both R", taken together, form a ring; wherein any alkyl, aryl, or ring may be substituted with —OH, alkyl, or halo.

7. The stabilized analogue of claim 1, wherein the stabilized analogue has reduced activity as compared to Caspase-3.

8. The stabilized analogue of claim 1, wherein the stabilized analogue has increased activity as compared to Caspase-3.

9. The stabilized analogue of claim 1, wherein the first Protein X and the second Protein X has at least 80% sequence identity to CAC88866.1.

10. The stabilized analogue of claim 1, wherein the first Protein X and the second Protein X has at least 85% sequence identity to CAC88866.1.

11. The stabilized analogue of claim 1, wherein the first Protein X and the second Protein X has at least 90% sequence identity to CAC88866.1.

12. The stabilized analogue of claim 1, wherein the first Protein X and the second Protein X has at least 95% sequence identity to CAC88866.1.

13. A method comprising the step of contacting a compound of Formula I or a compound of Formula II with a first Protein X and a second Protein X under conditions suitable for cross-linking the first Protein X to the second Protein X, thereby cross-linking the first Protein X to the second Protein X, wherein
the first Protein X comprises a first cysteine residue and has at least 80%, 85%, 86%, 87%, 88%, 89%, 90%, 91%, 92%, 93%, 94%, 95%, 96%, 97%, 98%, 99%, or 100% sequence identity to CAC88866.1;
the second Protein X comprises a second cysteine residue and has at least 80%, 85%, 86%, 87%, 88%, 89%, 90%, 91%, 92%, 93%, 94%, 95%, 96%, 97%, 98%, 99%, or 100% sequence identity to CAC88866.1;
the compound of Formula I is

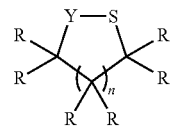

I wherein
Y is S, S=O, or S(=O)$_2$;
n is 0, 1, 2, 3, or 4; and
R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
R' is alkyl or aryl; and
the compound of Formula II is

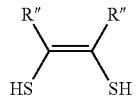

II wherein
R" is —H, alkyl, or aryl, or both R", taken together, form a ring; wherein any alkyl, aryl, or ring may be substituted with —OH, alkyl, or halo.

14. The method of claim 13, wherein the first Protein X and the second Protein X is CAC88866.1; and the compound is a compound of Formula I

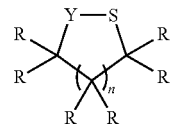

I wherein
Y is S, S=O, or S(=O)$_2$;
n is 0, 1, 2, 3, or 4; and
R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
R' is alkyl or aryl.

15. The method of claim 13, wherein the compound is a compound of Formula I; and the compound is selected from:

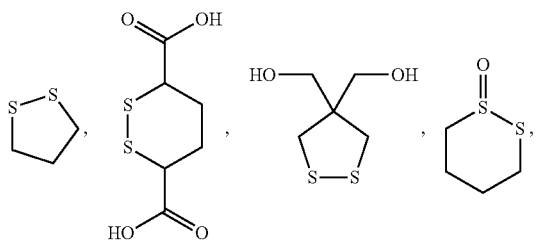

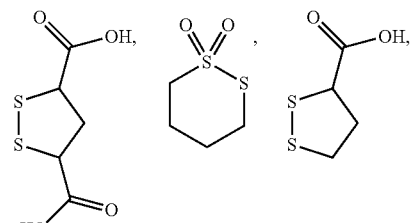

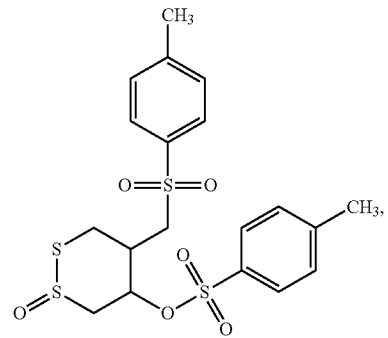

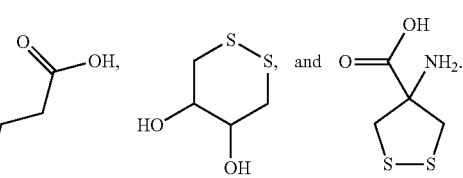

16. The method of claim 13, wherein the first Protein X and the second Protein X have at least 80%, 85%, 86%, 87%, 88%, 89%, 90%, 91%, 92%, 93%, 94%, 95%, 96%, 97%, 98%, 99%, or 100% sequence identity to CAC88866.1; and the compound is a compound of Formula II

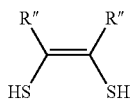
II wherein

R″ is —H, alkyl, or aryl, or both R″, taken together, form a ring; wherein any alkyl, aryl, or ring may be substituted with —OH, alkyl, or halo.

17. The method of claim 13, wherein the compound is a compound of Formula II, and the compound is

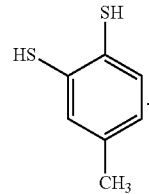

18. The method of claim 13, wherein the first Protein X and the second Protein X has at least 80% sequence identity to CAC88866.1.

19. The method of claim 13, wherein the first Protein X and the second Protein X has at least 85% sequence identity to CAC88866.1.

20. The method of claim 13, wherein the first Protein X and the second Protein X has at least 90% sequence identity to CAC88866.1.

21. The method of claim 13, wherein the first Protein X and the second Protein X has at least 95% sequence identity to CAC88866.1.

* * * * *

UNITED STATES PATENT AND TRADEMARK OFFICE
CERTIFICATE OF CORRECTION

PATENT NO. : 10,711,261 B2
APPLICATION NO. : 15/753319
DATED : July 14, 2020
INVENTOR(S) : Jeffrey N. Agar and Joseph Salisbury It is certified that error appears in the above-identified patent and that said Letters Patent is hereby corrected as shown below:

In the Claims

Column 37, Line 61, Insert the missing "O":

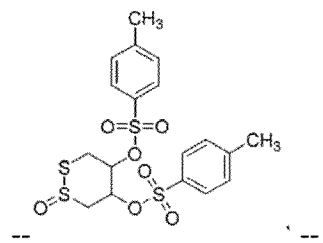

Column 40, Line 48, Insert the missing "O":

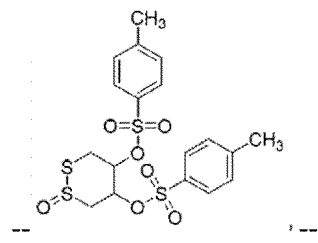

Signed and Sealed this
Twentieth Day of October, 2020

Andrei Iancu
*Director of the United States Patent and Trademark Office*